(12) United States Patent
Sinzger et al.

(10) Patent No.: US 11,390,661 B2
(45) Date of Patent: Jul. 19, 2022

(54) HCMV ENTRY INHIBITORS

(71) Applicant: AiCuris Anti-Infective Cures GmbH, Wuppertal (DE)

(72) Inventors: Christian Sinzger, Reutlingen (DE); Cora Stegmann, Ulm (DE); Kerstin Laib Sampaio, Dettingen (DE); Barbara Adler, Munich (DE)

(73) Assignee: AiCuris Anti-Infective Cures GmbH, Wuppertal (DE)

( * ) Notice: Subject to any disclaimer, the term of this patent is extended or adjusted under 35 U.S.C. 154(b) by 57 days.

(21) Appl. No.: 16/313,198

(22) PCT Filed: Jun. 27, 2017

(86) PCT No.: PCT/EP2017/065902
§ 371 (c)(1),
(2) Date: Dec. 26, 2018

(87) PCT Pub. No.: WO2018/002081
PCT Pub. Date: Jan. 4, 2018

(65) Prior Publication Data
US 2019/0161532 A1    May 30, 2019

(30) Foreign Application Priority Data
Jun. 27, 2016    (EP) .................................. 16176520

(51) Int. Cl.
| C07K 14/71 | (2006.01) |
| A61K 38/17 | (2006.01) |
| A61P 31/22 | (2006.01) |
| C07K 16/28 | (2006.01) |
| A61K 39/00 | (2006.01) |
| C12N 15/113 | (2010.01) |
| C07K 19/00 | (2006.01) |

(52) U.S. Cl.
CPC ............ *C07K 14/71* (2013.01); *A61K 38/179* (2013.01); *A61K 39/0005* (2013.01); *A61P 31/22* (2018.01); *C07K 16/2863* (2013.01); *C12N 15/1138* (2013.01); *C07K 19/00* (2013.01); *C07K 2317/92* (2013.01); *C07K 2319/30* (2013.01); *C07K 2319/74* (2013.01); *C12N 2310/14* (2013.01)

(58) Field of Classification Search
CPC .......... C07K 2319/30; C07K 16/2863; C07K 14/71
See application file for complete search history.

(56) References Cited

U.S. PATENT DOCUMENTS

| 6,667,173 B2 * | 12/2003 | Kazlauskas | ........ A61K 38/1858 |
|---|---|---|---|
| | | | 435/320.1 |
| 8,128,929 B2 | 3/2012 | Loizos et al. | |
| 8,435,510 B2 | 5/2013 | Cobbs et al. | |
| 8,802,106 B2 | 8/2014 | Melnik et al. | |
| 9,340,788 B2 | 5/2016 | Cobbs et al. | |
| 9,434,769 B2 | 9/2016 | Melnik et al. | |
| 9,884,910 B2 | 2/2018 | Fromond et al. | |
| 2005/0239088 A1 * | 10/2005 | Shepard | .................... A61P 3/10 |
| | | | 435/6.14 |
| 2006/0234347 A1 | 10/2006 | Harding et al. | |
| 2008/0199438 A1 * | 8/2008 | Sueishi | .................... A61P 43/00 |
| | | | 514/1.1 |
| 2011/0311523 A1 | 12/2011 | Cobbs et al. | |
| 2013/0005648 A1 | 1/2013 | Melnik et al. | |
| 2014/0161811 A1 | 6/2014 | Cobbs et al. | |
| 2015/0119318 A1 | 4/2015 | Melnik et al. | |
| 2015/0232546 A1 | 8/2015 | Fromond et al. | |

FOREIGN PATENT DOCUMENTS

| WO | 2009/021150 A2 | 2/2009 |
| WO | 2011/053798 A2 | 5/2011 |
| WO | 2013/160359 A1 | 10/2013 |

OTHER PUBLICATIONS

Torrente et al., Mechanisms of PDGFRalpha promiscuity and PDGFRbeta specificity in association with PDGFB . Front Biosci. (Elite Ed). Jun. 1, 2015;7:434-446.*
Mahadevan et al., Structural Role of Extracellular Domain 1 of a-Platelet-derived Growth Factor (PDGF) Receptor for PDGF-AA and PDGF-BB Binding. 270 (46): 27595-27600, 1995.*
Sang et al., Transient Expression of Recombinant sPDGFRα-Fc in CHO DG44 Cells using 50-mL Orbitally Shaking Disposable Bioreactors. Protein and Peptide Letters 17 (7): 919-924, 2010.*
International Search Report dated Nov. 10, 2017 issued in corresponding PCT/EP2017/065902 application (9 pages).
A.L. Vanarsdall et al. "PDGF Receptor-alpha Does Not Promote HCMV Entry into Epithelial and Endothelial Cells but Increased Quantities Stimulate Entry by an Abnormal Pathway", PLOS Pathogens, vol. 8, Issue 9 (Sep. 2012) p. e1002905.
C. Cobbs et al., "HCMV Glycoprotein B is Expressed in Primary Glioblastomas and Enhances Growth and Invasiveness Via PDGFR-Alpha Activation", Oncotarget, vol. 5, No. 4 (2014) pp. 1091-1100.
D Torrente et al., "Mechanisms of PDGFRalpha Promiscuity and PDGFRbeta Specificity in Association with PDGFB", Frontiers in Bioscience, vol. 7 (2015) pp. 434-446.
L. Soroceanu et al., "Platelet-Derived Growth Factor-alpha Receptor Activation is Required for Human Cytomegalovirus Infection", Nature, vol. 455, No. 7211 (2008) pp. 391-395.

(Continued)

*Primary Examiner* — Ruixiang Li
(74) *Attorney, Agent, or Firm* — Millen White Zelano & Branigan, PC; Brion P. Heaney

(57) ABSTRACT

Subject matter of the present invention is a soluble PDGFR-alpha-Fc chimera or a PDGFR-alpha derived peptide or an anti-PDGFR-alpha antibody or a PDGFR-alpha antibody fragment or anti-PDGFR-alpha non-Ig scaffold for inhibiting HCMV entry for use in a method of treatment in a subject that has been infected by HCMV or for use in a method of prophylaxis of HCMV infection in a subject that has not yet been infected by HCMV.

Figure 1:
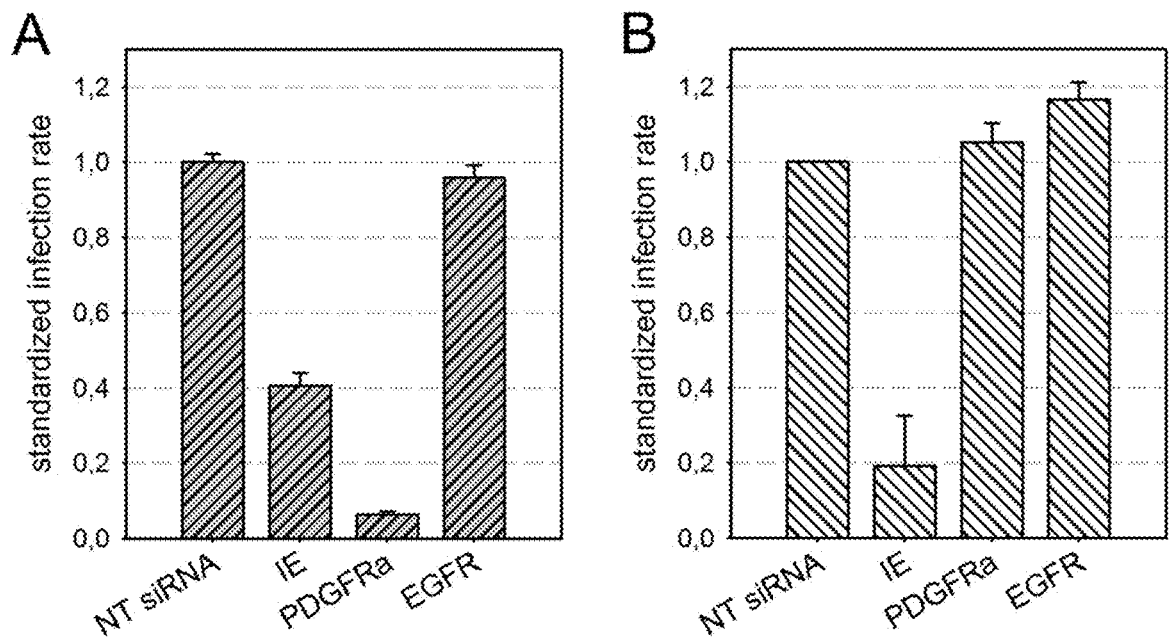

9 Claims, 10 Drawing Sheets
Specification includes a Sequence Listing.

(56) References Cited

OTHER PUBLICATIONS

N. Loizos et al., "Targeting the Platelet-Derived Growth Factor Receptor alpha with a Neutralizing Human Monoclonal Antibody Inhibits the Growth of Tumor Xenografts: Implications as a Potential Therapeutic Target", Molecular Cancer Therapeutics, vol. 4, No. 3 (2005) pp. 369-379.
"Recombinant Human PDGFR[alpha] Fc Chimera", XP055328558—Retrieved from the Internet—(Jan. 1, 2008) p. 2667.
M.A. Heidaran et al., "Deletion or Substitution within the alpha Platelet-Derived Growth Factor Receptor Kinase Insert Domain: Effects on Functional Coupling with Intracellular Signaling Pathways", Molecular and Cellular Biology, vol. 11, No. 1 (1991) pp. 134-142.

\* cited by examiner

HCMV ENTRY INHIBITORS

Subject matter of the present invention is a soluble PDGFR-alpha-Fc chimera or a PDGFR-alpha derived peptide or an anti-PDGFR-alpha antibody or a PDGFR-alpha antibody fragment or anti-PDGFR-alpha non-Ig scaffold for inhibiting HCMV entry for use in a method of treatment in a subject that has been infected by HCMV or for prophylaxis of HCMV infection in a subject that has not yet been infected by HCMV.

Human cytomegalovirus (HCMV) is a pathogenic human beta-herpesvirus, which like other beta-herpesviruses can only replicate in its specific host. Primary infection is followed by lifelong latent persistence and occasional reactivation of the virus, which usually goes unnoticed by the infected individual. However, under conditions of insufficient immune responses, HCMV can cause severe or even life threatening disease, e.g. in AIDS patients, transplant recipients, and infected fetuses after intrauterine infection. Antiviral drugs are available but associated with significant adverse effects and the development of resistance (3, 15). Therefore, alternative treatment options are desired.

One powerful antiviral strategy is the inhibition of entry into the cell, and its effectiveness against HCMV is exemplified by the neutralizing activity of anti-HCMV antibodies (5, 12, 13, 23, 26, 30, 31, 36). While the therapeutic use of antibodies may be limited as they are difficult to engineer, other entry inhibitors are also conceivable for HCMV. In case of HIV, small molecules and peptides have already been approved for antiviral therapy (17); a peptide-based entry inhibitor against Hepatitis B virus is in clinical trial (34); and with picorna viruses, an Fc-CAR fusion protein inhibits viral entry and is effective in animal models, but has not yet been developed for clinical use (14, 29, 41).

HCMV is an enveloped virus and has to fuse its membrane with the host membrane for penetration of the nucleocapsid into the cytoplasm, from where it is then transported to the nucleus and releases the viral genome into the nucleoplasm. Several glycoprotein complexes in the envelope of HCMV particles have been described that contribute to entry of HCMV into its target cells and are therefore potential targets of entry inhibitors (7, 8, 20, 22, 24, 27). In analogy to other herpesviruses, homotrimers of glycoprotein B (gB) are assumed to exert the fusion between viral envelope and cellular membrane, while heterotrimers of gH, gL and gO are necessary to promote this fusion process (4, 6, 9, 18, 42). On certain cell types including endothelial and epithelial cells, a pentameric complex is required in addition for effective entry, which consists of gH, gL, and three accessory proteins from the viral UL128 gene (1, 2, 16, 37, 42).

On the cellular side, numerous proteins have been proposed as entry receptors of HCMV, including various integrins, the epithelial growth factor receptor (EGFR) and the platelet-derived growth factor receptor alpha (PDGFR-alpha), but have been controversially discussed (11, 21, 33, 35, 38, 39) (reviewed in (2)).

The inventors surprisingly and unexpectedly found that the extracellular part of PDGFR-alpha is a highly potent entry inhibitor of HCMV in either cell type, and peptides derived from this molecule are also effective, thus providing a rationale for the development of PDGFR-alpha based anti-HCMV therapeutics.

Thus, subject matter of the present invention is a soluble PDGFR-alpha-Fc chimera for inhibiting HCMV entry for use in a method of treatment in a subject that has been infected by HCMV or for prophylaxis of HCMV infection in a subject that has not yet been infected by HCMV, wherein said soluble PDGFR-alpha-Fc chimera comprises a PDGFR-alpha sequence selected from the group comprising:

```
I. SEQ ID No. 2 (aa 24 to aa 524 of SEQ ID No. 1):
QLSLPSILPNENEKVVQLNSSFSLRCFGESEVSWQYPMSEEESSDVEIRN

EENNSGLFVTVLEVSSASAAHTGLYTCYYNHTQTEENELEGRHIYIYVPD

PDVAFVPLGMTDYLVIVEDDDSAIIPCRTTDPETPVTLHNSEGVVPASYD

SRQGFNGTFTVGPYICEATVKGKKFQTIPFNVYALKATSELDLEMEALKT

VYKSGETIVVTCAVFNNEVVDLQWTYPGEVKGKGITMLEEIKVPSIKLVY

TLTVPEATVKDSGDYECAARQATREVKEMKKVTISVHEKGFIEIKPTFSQ

LEAVNLHEVKHFVVEVRAYPPPRISWLKNNLTLIENLTEITTDVEKIQEI

RYRSKLKLIRAKEEDSGHYTIVAQNEDAVKSYTFELLTQVPSSILDLVDD

HHGSTGGQTVRCTAEGTPLPDIEWMICKDIKKCNNETSWTILANNVSNII

TEIHSRDRSTVEGRVTFAKVEETIAVRCLAKNLLGAENRELKLVAPTLRS

E,
```

II. a sequence having 90% or more identity to SEQ ID No. 2

III. a sequence that is a truncated sequence of SEQ ID No. 2 or a sequence having 90% or more identity to said truncated SEQ ID No. 2, said sequence having at least 45 amino acids, and IV. variants of sequences according to the aforementioned items I., II., III., with substitutions at one or more of the following positions (numbering is adhered to SEQ ID. No. 1):

Ile 30, Glu-52, Ser-66, Ser-67, Asp-68, Leu-80, Ser-89, His-162, Pro-169, Asp-173, Ile-188, Val-193, Lys-194, Glu-213, Lys-304, Thr-320, His-334, Arg-340, Ile-373, Lys-378, Ala-396, Ala-401, Thr-436, Thr-440, Ile-453, Val-469, Ile-476, Ser-478, Asp-480, Ser-482, Arg-487.

Percentage of sequence identity is calculated for the shortened peptide in case of truncated peptide (i.e. variants). Introduction of additional amino acids are handled as gap in the original sequence, deletions are handled as gap in the modified peptide for calculation of sequence identity. A truncated sequence of a Sequence is a fragment of said Sequence.

Truncated sequence of SEQ ID No. 2 means the sequence of SEQ ID No. 2, wherein certain amino acid (stretches) within said sequence are deleted. SEQ ID No. 3 is e.g. a truncated sequence of SEQ ID No. 2. A truncated sequence of SEQ ID No. 2 is a fragment of said sequence.

A sequence that is a truncated sequence of SEQ ID No. 2 or a sequence having 90% or more identity to said truncated SEQ ID No. 2 has at least 45 amino acids, preferably at least 80 amino acids, more preferably at least 100 amino acids, even more preferred at least 150 amino acids.

"Soluble PDGFR-alpha-Fc chimera" means that the respective PDGFR-alpha derivate can be dissolved in biocompatible solutions, preferably saline, at a concentration of at least 100 µg/ml.

"HCMV" means Human cytomegalovirus.

Also, subject matter of the present invention is a soluble PDGFR-alpha-Fc chimera for inhibiting HCMV entry for use in a method of treatment in a subject that has been infected by HCMV or for prophylaxis of HCMV infection in a subject that has not yet been infected by HCMV according to the invention, wherein said soluble PDGFR-alpha-Fc chimera inhibits HCMV entry.

Inhibition of HCMV entry is determined by measuring the reduction of infectivity of HCMV in cell culture assays, as follows:

Infectious cell free HCMV preparations (corresponding to a multiplicity of infection of 1) are pre-incubated with the substance (at variable concentrations) for 2 h at 37° C. The pre-incubated mixture of HCMV and substance is added to cell cultures of choice, including at least a culture of human primary fibroblasts and a culture of human endothelial cells. Cells are incubated with the mixture for 2 h at 37° C. The mixture of HCMV and substance is then replaced with the appropriate cell culture medium and cells are further incubated for at least 16 h at 37° C. HCMV infection of the cells is detected by immunostaining of HCMV immediate early antigens (pUL122/123) with indirect immunofluorescence. The ratio of HCMV-IE antigen-positive cells per total cells is calculated as a readout for the efficiency of viral entry. The $EC_{50}$ is determined as the concentration of the substance (given in ng/ml) that reduces the fraction of infected cells in any of the tested cell types by 50% as compared to controls in which HCMV has been pre-incubated with medium (minimal essential medium with 5% fetal calf serum) instead of the substance.

If the substance is a PDGFR-alpha-Fc chimera, it is regarded effective if the $EC_{50}$ in the assay described above is lower than 1000 ng/ml, preferably lower than 100 ng/ml.

If the substance is a peptide, it is regarded effective if the $EC_{50}$ in the assay described above is lower than 10 nmol/ml, preferably lower than 0.5 nmol/ml.

If the substance is an antibody, it is regarded effective if the $EC_{50}$ in the assay described above is lower than 5 µg/ml, preferably lower than 0.5 µg/ml.

In one embodiment of the invention a soluble PDGFR-alpha-Fc chimera is used for inhibiting HCMV entry in a method of treatment in a subject that has been infected by HCMV or used for prophylaxis of HCMV infection in a method of treatment of a subject that has not yet been infected by HCMV according the invention wherein said soluble PDGFR-alpha-Fc chimera has at least one of the following mutations or deletions within SEQ ID No. 2 (numbering is adhered to SEQ ID No. 1):
  i. Deletion of aa 150-189,
  ii. Deletion of aa 150-234,
  iii. Deletion of aa 150-290,
  iv. Deletion of aa 150-524,
  v. Deletion of aa 24-100 and deletion of aa 150-234,
  vi. SEQ ID No. 2 having at least one point mutation in at least one of the protein regions as specified above under items i., ii., iii., iv., v . . . .

In another embodiment of the invention a soluble PDGFR-alpha-Fc chimera is used that is suitable for inhibiting HCMV entry in a method of treatment in a subject that has been infected by HCMV or used for prophylaxis of HCMV infection in a method of treatment of a subject that has not yet been infected by HCMV according the invention wherein said soluble PDGFR-alpha-Fc chimera has at least one of the following mutations or deletions within SEQ ID No. 2 (numbering is adhered to SEQ ID No. 1):
  i. Deletion of amino acids M133-I139 (optionally having additional deletions at the N- and/or C-termini of at least one or at least two or at least three N-terminal amino acids and/or at least one or at least two or at least three or at least four or at least five C-terminal amino acids, wherein each of the respective combinations of additional deletions, e.g., one N-terminal plus one C-terminal deletions; two N-terminal plus three C-terminal deletions, three N-terminal and five C-terminal deletions shall are given here as examples for all possible combinations of additional deletions at the respective ends of amino acids M133-I139; further it is possible also to delete one or two or three or four or five amino acids less than amino acids M133-I139 at the N-terminus and/or the C-terminus, wherein all possible combinations of fewer deleted amino acids are possible, provided that at least one amino acid remains deleted in the stretch of amino acids M133-I139),
  ii. Deletion of amino acids V184-G185 (optionally having additional deletions at the N- and/or C-termini of at least one or at least two or at least three N-terminal amino acids and/or at least one or at least two or at least three or at least four or at least five C-terminal amino acids, wherein each of the respective combinations of additional deletions, e.g., one N-terminal plus one C-terminal deletions; two N-terminal plus three C-terminal deletions, three N-terminal and five C-terminal deletions shall be given here as examples for all possible combinations of additional deletions at the respective ends of amino acids V184-G185; Furthermore, it is possible also to delete one amino acid less than amino acids V184-G185 at the N-terminus and/or the C-terminus, wherein all possible combinations of fewer deleted amino acids are possible, provided that at least one amino acid remains deleted in the stretch of amino acids V184-G185),
  iii. Deletion of amino acids N204-Y206 (optionally having additional deletions at the N- and/or C-termini of at least one or at least two or at least three N-terminal amino acids and/or at least one or at least two or at least three or at least four or at least five C-terminal amino acids, wherein each of the respective combinations of additional deletions, e.g., one N-terminal plus one C-terminal deletions; two N-terminal plus three C-terminal deletions, three N-terminal and five C-terminal deletions shall are given here as examples for all possible combinations of additional deletions at the respective ends of amino acids N204-Y206; furthermore, it is possible also to delete one or two amino acid less than amino acids N204-Y206 at the N-terminus and/or the C-terminus, wherein all possible combinations of fewer deleted amino acids are possible, provided that at least one amino acid remains deleted in the stretch of amino acids N204-Y206);
  iv. Deletion of amino acids N240-L245 (optionally having additional deletions at the N- and/or C-termini of at least one or at least two or at least three N-terminal amino acids and/or at least one or at least two or at least three or at least four or at least five C-terminal amino acids, wherein each of the respective combinations of additional deletions, e.g., one N-terminal plus one C-terminal deletions; two N-terminal plus three C-terminal deletions, three N-terminal and five C-terminal deletions shall are given here as examples for all possible combinations of additional deletions at the respective ends of amino acids N240-L245; further it is possible also to delete one or two or three or four or five amino acids less than amino acids N240-L245 at the N-terminus and/or the C-terminus, wherein all possible combinations of fewer deleted amino acids are possible, provided that at least one amino acid remains deleted in the stretch of amino acids N240-L245), v. Deletion of amino acids T259-E262 (optionally having additional deletions at the N- and/or C-termini of at least one or at least two or at least three N-terminal amino acids and/or at least one or at least two or at least three or at least four or at least five C-terminal amino acids, wherein each of the respective combinations of additional deletions, e.g., one N-terminal plus one C-terminal deletions; two N-terminal plus three C-terminal deletions, three N-terminal and five C-terminal deletions shall are given here as examples for all possible combinations of additional deletions at the respective ends of amino acids T259-E262; further it is possible also to delete one or two or three or four amino acids less than amino acids T259-E262 at the N-terminus and/or the C-terminus, wherein all possible combinations of fewer deleted amino acids are possible, provided that at least one amino acid remains deleted in the stretch of amino acids T259-E262);

vi. Deletion of amino acids K270-T273 (optionally having additional deletions at the N- and/or C-termini of at least one or at least two or at least three N-terminal amino acids and/or at least one or at least two or at least three or at least four or at least five C-terminal amino acids, wherein each of the respective combinations of additional deletions, e.g., one N-terminal plus one C-terminal deletions; two N-terminal plus three C-terminal deletions, three N-terminal and five C-terminal deletions shall are given here as examples for all possible combinations of additional deletions at the respective ends of amino acids K270-T273; further it is possible also to delete one or two or three amino acids less than amino acids K270-T273 at the N-terminus and/or the C-terminus, wherein all possible combinations of fewer deleted amino acids are possible, provided that at least one amino acid remains deleted in the stretch of amino acids K270-T273);

vii. Deletion of amino acids Q294-E298 (optionally having additional deletions at the N- and/or C-termini of at least one or at least two or at least three N-terminal amino acids and/or at least one or at least two or at least three or at least four or at least five C-terminal amino acids, wherein each of the respective combinations of additional deletions, e.g., one N-terminal plus one C-terminal deletions; two N-terminal plus three C-terminal deletions, three N-terminal and five C-terminal deletions shall are given here as examples for all possible combinations of additional deletions at the respective ends of amino acids Q294-E298; further it is possible also to delete one or two or three or four amino acids less than amino acids Q294-E298 at the N-terminus and/or the C-terminus, wherein all possible combinations of fewer deleted amino acids are possible, provided that at least one amino acid remains deleted in the stretch of amino acids Q294-E298);

viii. SEQ ID No. 2 having at least one point mutation in at least one of the protein regions as specified above under items i., ii., iii., iv., v., vi, or vii.

One embodiment is a soluble truncated or mutated version of PDGFR-alpha-Fc chimera that is used for inhibiting HCMV entry in a method of treatment in a subject that has been infected by HCMV or for use in prophylaxis of HCMV infection in a subject that has not yet been infected by HCMV according to the invention, wherein said soluble truncated or mutated version of PDGFR-alpha-Fc chimera inhibits HCMV entry and shows reduced ability to inhibit the biological activity of PDGF-type growth factors as compared to the inhibitory effect of wild type chimeras.

A soluble truncated or mutated version of PDGFR-alpha-Fc chimera may be selected from the group comprising:

I. a sequence having 90% or more identity to SEQ ID No. 2,

II. a sequence that is a truncated sequence of SEQ ID No. 2 or a sequence having 90% or more identity to said truncated SEQ ID No. 2 said sequence having at least 45 amino acids, III. variants of sequences according to the yet aforementioned items I. and II., with substitutions at one or more of the following positions (numbering is adhered to SEQ ID. No. 1):

Ile-30, Glu-52, Ser-66, Ser-67, Asp-68, Leu-80, Ser-89, His-162, Pro-169, Asp-173, Ile-188, Val-193, Lys-194, Glu-213, Lys-304, Thr-320, His-334, Arg-340, Ile-373, Lys-378, Ala-396, Ala-401, Thr-436, Thr-440, Ile-453, Val-469, Ile-476, Ser-478, Asp-480, Ser-482, Arg-487.

A wild type chimera is a chimera of:

```
SEQ ID No. 2 (aa 24 to aa 524 of SEQ ID No. 1):
QLSLPSILPNENEKVVQLNSSFSLRCFGESEVSWQYPMSEEESSDVEIRN

EENNSGLFVTVLEVSSASAAHTGLYTCYYNHTQTEENELEGRHIYIYVPD

PDVAFVPLGMTDYLVIVEDDDSAIIPCRTTDPETPVTLHNSEGVVPASYD

SRQGFNGTFTVGPYICEATVKGKKFQTIPFNVYALKATSELDLEMEALKT

VYKSGETIVVTCAVFNNEVVDLQWTYPGEVKGKGITMLEEIKVPSIKLVY

TLTVPEATVKDSGDYECAARQATREVKEMKKVTISVHEKGFIEIKPTFSQ

LEAVNLHEVKHFVVEVRAYPPPRISWLKNNLTLIENLTEITTDVEKIQEI

RYRSKLKLIRAKEEDSGHYTIVAQNEDAVKSYTFELLTQVPSSILDLVDD

HHGSTGGQTVRCTAEGTPLPDIEWMICKDIKKCNNETSWTILANNVSNII

TEIHSRDRSTVEGRVTFAKVEETIAVRCLAKNLLGAENRELKLVAPTLRS

E
and

SEQ ID No. 8 (6 amino acids which are a linker
between SEQ ID No. 1 and human Fc):
LTVAGS

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPGK
```

The biological activity of PDGF-type growth factors is determined as the induction of cell proliferation in PDGF-sensitive cell lines such as human fibroblasts. The ability to inhibit this biological activity is determined as the degree by which induction of proliferation is reduced when PDGFs have been pre-incubated with the substance for 2 h at 37° C., as compared to PDGFs alone. The degree of proliferation can be measured in standard MTT assay as described previously (19). In addition or alternatively the direct binding of PDGF-type growth factors to the soluble truncated or mutated version of PDGFR-alpha-Fc chimera (and the PDGFRalpha derived peptides) is measured via suitable techniques e.g. thermophorese using the Nanotemper technology; Biacore, and the like.

Also, subject matter of the present invention is a soluble PDGFR-alpha-Fc chimera that is used for inhibiting HCMV entry in a method of treatment in a subject that has been infected by HCMV or for use in prophylaxis of HCMV infection in a subject that has not yet been infected by HCMV according to the present invention, wherein said soluble PDGFR-alpha-Fc chimera is administered to a pregnant woman who is infected by HCMV, or a congenitally HCMV-infected child, or a bone marrow transplant recipient infected with HCMV, or a solid organ transplant recipients infected with HCMV. It may be also used in a method of treatment in a subject that has been infected by HCMV, wherein said soluble PDGFR-alpha-Fc chimera is administered to said subject who is also HIV-infected.

In one embodiment a soluble PDGFR-alpha-Fc chimera according to the present invention comprises a sequence selected from the group comprising:

SEQ ID No. 3:
QLSLPSILPNENEKVVQLNSSFSLRCFGESEVSWQYPMSEEESSDVEIRN
EENNSGLFVTVLEVSSASAAHTGLYTCYYNHTQTEENELEGRHIYIYVPD
PDVAFVPLGMTDYLVIVEDDDSAIIPEATVKGKKFQTIPFNVYALKATSE
LDLEMEALKTVYKSGETIVVTCAVFNNEVVDLQWTYPGEVKGKGITMLEE
IKVPSIKLVYTLTVPEATVKDSGDYECAARQATREVKEMKKVTISVHEKG
FIEIKPTFSQLEAVNLHEVKHFVVEVRAYPPPRISWLKNNLTLIENLTEI
TTDVEKIQEIRYRSKLKLIRAKEEDSGHYTIVAQNEDAVKSYTFELLTQV
PSSILDLVDDHHGSTGGQTVRCTAEGTPLPDIEWMICKDIKKCNNETSWM
ANNVSNIITEIHSRDRSTVEGRVTFAKVEETIAVRCLAKNLLGAENRELK
LVAPTLRSE,

SEQ ID No. 4:
QLSLPSILPNENEKVVQLNSSFSLRCFGESEVSWQYPMSEEESSDVEIRN
EENNSGLFVTVLEVSSASAAHTGLYTCYYNHTQTEENELEGRHIYIYVPD
PDVAFVPLGMTDYLVIVEDDDSAIIPCAVFNNEVVDLQWTYPGEVKGKGI
TMLEEIKVPSIKLVYTLTVPEATVKDSGDYECAARQATREVKEMKKVTIS
VHEKGFIEIKPTFSQLEAVNLHEVKHFVVEVRAYPPPRISWLKNNLTLIE
NLTEITTDVEKIQEIRYRSKLKLIRAKEEDSGHYTIVAQNEDAVKSYTFE
LLTQVPSSILDLVDDHHGSTGGQTVRCTAEGTPLPDIEWMICKDIKKCNN
ETSWTILANNVSNIITEIHSRDRSTVEGRVTFAKVEETIAVRCLAKNLLG
AENRELKLVAPTLRSE,

SEQ ID No. 5:
QLSLPSILPNENEKVVQLNSSFSLRCFGESEVSWQYPMSEEESSDVEIRN
EENNSGLFVTVLEVSSASAAHTGLYTCYYNHTQTEENELEGRHIYIYVPD
PDVAFVPLGMTDYLVIVEDDDSAIIPAARQATREVKEMKKVTISVHEKGF
IEIKPTFSQLEAVNLHEVKHFVVEVRAYPPPRISWLKNNLTLIENLTEIT
TDVEKIQEIRYRSKLKLIRAKEEDSGHYTIVAQNEDAVKSYTFELLTQVP
SSILDLVDDHHGSTGGQTVRCTAEGTPLPDIEWMICKDIKKCNNETSWTI
LANNVSNIITEIHSRDRSTVEGRVTFAKVEETIAVRCLAKNLLGAENREL
KLVAPTLRSE,

SEQ ID No. 6:
QLSLPSILPNENEKVVQLNSSFSLRCFGESEVSWQYPMSEEESSDVEIRN
EENNSGLFVTVLEVSSASAAHTGLYTCYYNHTQTEENELEGRHIYIYVPD
PDVAFVPLGMTDYLVIVEDDDSAIIP,

SEQ ID No. 7:
YYNHTQTEENELEGRHIYIYVPDPDVAFVPLGMTDYLVIVEDDDSAIIP.

In one embodiment of the present invention a soluble PDGFR-alpha-Fc chimera of the present invention comprises further a sequence of human Fc that is SEQ ID No. 8:

LTVAGSDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDK
SRWQQGNVFSCSVMHEALHNHYTQKSLSLSPGK.

Subject matter of the present invention is a PDGFR-alpha derived peptide for inhibiting HCMV entry that is for use in a method of treatment in a subject that has been infected by HCMV or for use in a method prophylaxis of HCMV infection in a subject that has not yet been infected by HCMV, wherein said peptide is selected from a group comprising SEQ ID No. 9 (between 10 aa and 60 aa in length), SEQ ID No. 10, SEQ ID No. 11, or SEQ ID NO: 12, or SEQ ID No. 13, or consists of parts of the following sequences:
  I. SEQ ID No. 9 that is VLEVSSASAAHTGLYT-CYYNHTQTEENELE GRHIYIYVPDPDVAFVPLGMTDYLVIVEDDD-SAIIPCRTTDPETPVTLHN,
  II. SEQ ID No. 10, also referred to as IK40, that is IKVPSIKLVYTLTVPEATVKDSGDYECAARQAT-REVKEMK,
  III. SEQ ID No. 11, also referred as GD30, that is GRHIYIYVPDPDVAFVPLGMTDYLVIVEDD),
  IV. SEQ ID No. 12 (also referred to as GT40) that is GRHIYIYVPDPDVAFVPLGMTDYLVIVEDDD-SAIIPCRTT,
  V. SEQ ID No. 13 (also referred to as NV40) that is NVYALKATSELDLEMEALKTVYKSGETIVVT-CAVFNNEVV,
  VI. a peptide fragment of SEQ ID No. 9, SEQ ID No. 10, SEQ ID NO: 11, or SEQ ID No. 12, or SEQ ID No. 13, any of these having at least 10 amino acids, and
  VII. a variant of the yet aforementioned items I., to VI. that exhibits at least 80% sequence identity to the peptide having the sequence of SEQ ID No. 9, SEQ ID No. 10, SEQ ID NO: 11, or SEQ ID No. 12, or SEQ ID No. 13, or a peptide that exhibits at least 80% sequence identity to the peptide fragment of SEQ ID No. 9, SEQ ID No. 10, SEQ ID NO: 11, SEQ ID No. 12, or SEQ ID No. 13, having at least 10 amino acids.

Subject matter of the present invention is a PDGFR-alpha derived peptide for inhibiting HCMV entry used for a method of treatment in a subject that has been infected by HCMV or for use in a method of prophylaxis of HCMV infection in a subject that has not yet been infected by HCMV according to the present invention, wherein said peptide inhibits HCMV entry. In some embodiments, said PDGFR-alpha derived peptide is a fragment derived from domain 1, domain 2, or domain 3 of PDGFR-alpha as exemplified by the peptides according to SEQ ID Nos. 9 to 13.

Subject matter of the present invention is a soluble PDGFR-alpha derived peptide for inhibiting HCMV entry used in a method of treatment in a subject that has been infected by HCMV or for use in a method of prophylaxis of HCMV infection in a subject that has not yet been infected by HCMV according to the present invention, wherein said peptide is administered to a pregnant woman that is infected by HCMV or a congenitally HCMV-infected child, or a bone marrow transplant recipient infected with HCMV or at risk of HCMV infection, or a solid organ transplant recipient infected with HCMV or at risk with HCMV infection. In some embodiments, said PDGFR-alpha derived peptide is a fragment derived from domain 1, domain 2, or domain 3 of PDGFR-alpha as exemplified by the peptides according to SEQ ID Nos. 9 to 13.

Subject matter of the present invention are also delivery vectors for transferring a nucleic acid sequence encoding a PDGFR-alpha derived peptide or fragment thereof suitable for inhibiting HCMV entry, wherein said nucleic acid comprises a signal sequence that enables the packing of said peptide or fragment thereof into vesicles, wherein the peptide or fragment is released from the cells to bind to HCMV and inhibit infection of target cells. The object of the present invention is, thus, to provide delivery vectors for transferring a nucleic acid sequence to a cell in vitro, ex vivo or in vivo. Object of the invention is in particular a vector-based therapy for treatment and/or prophylaxis and/or prevention of spreading in a host of HCMV infection with PDGFR-alpha derived peptides or fragments thereof. The inventive delivery vectors comprising a nucleic acid encoding PDGFR-alpha derived peptides or fragments thereof shall transduce host cells, which are capable of expressing the peptides and which are suitable for expression of said peptides to thereby inhibiting HCMV infection, attachment, membrane fusion or propagation of the virus. This means as an example that said delivery vector may comprise a DNA sequence encoding a PDGFR-alpha peptide as defined herein and expresses the respective peptide(s) or fragment(s) thereof at a concentration that is sufficient to inhibit infections of target cells. In some embodiments, said PDGFR-alpha derived peptide is a fragment derived from domain 1, domain 2, or domain 3 of PDGFR-alpha as exemplified by the peptides according to SEQ ID Nos. 9 to 13.

The delivery vectors produced according to the present invention are useful for the delivery of nucleic acids to cells in vitro, ex vivo, and in vivo. In particular, the delivery vectors can be advantageously employed to deliver or transfer nucleic acids to animal, more preferably mammalian, cells.

Suitable vectors include viral vectors (e.g., retrovirus, lentivirus, alphavirus; vaccinia virus; adenovirus, adeno-associated virus, or herpes simplex virus), lipid vectors, polylysine vectors, synthetic polyamino polymer vectors that are used with nucleic acid molecules, such as plasmids, and the like.

Any viral vector that is known in the art can be used in the present invention. Examples of such viral vectors include, but are not limited to vectors derived from: Adenoviridae; Birnaviridae; Bunyaviridae; Caliciviridae, Capillovirus group; Carlavirus group; Carmovirus virus group; Group Caulimovirus; Closterovirus Group; *Commelina* yellow mottle virus group; Comovirus virus group; Coronaviridae; PM2 phage group; Corcicoviridae; Group Cryptic virus; group Cryptovirus; Cucumovirus virus group Family ([PHgr]6 phage group; Cysioviridae; Group Carnation ringspot; Dianthovirus virus group; Group Broad bean wilt; Fabavirus virus group; Filoviridae; Flaviviridae; Furovirus group; Group Germinivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picomaviridae; Plasmaviridae; Prodoviridae; Polydnaviridae; Potexvirus group; Potyvirus; Poxviridae; Reoviridae; Retroviridae; Rhabdoviridae; Group Rhizidiovirus; Siphoviridae; Sobemovirus group; SSV 1-Type Phages; Tectiviridae; Tenuivirus; Tetraviridae; Group Tobamovirus; Group Tobravirus; Togaviridae; Group Tombusvirus; Group Tobovirus; Totiviridae; Group Tymovirus; and Plant virus satellites. Protocols for producing recombinant viral vectors and for using viral vectors for nucleic acid delivery can be found in (Ausubel et al., 1989) and other standard laboratory manuals (e.g., Rosenzweig et al. 2007). Particular examples of viral vectors are those previously employed for the delivery of nucleic acids including, for example, retrovirus, lentivirus, adenovirus, adeno-associated virus (AAV) and other parvoviruses, herpes virus, and poxvirus vectors. The term "parvovirus" as used herein encompasses the family Parvoviridae, including autonomous parvoviruses, densoviruses and dependoviruses. The term AAV includes all vertebrate variants especially of human, primate, other mammalian, avian or serpentine origin. The autonomous parvoviruses include members of the genera Parvovirus, Erythrovirus, Bocavirus, Densovirus, Iteravirus, and Contravirus. Exemplary autonomous parvoviruses include, but are not limited to, minute virus of mice, bovine parvovirus, canine parvovirus, chicken parvovirus, feline panleukopenia virus, feline parvovirus, goose parvovirus, HI parvovirus, muscovy duck parvovirus, bocavirus, bufavirus, tusavirus and B19 virus, and any other virus classified by the International Committee on Taxonomy of Viruses (ICTV) as a parvovirus. Other autonomous parvoviruses are known to those skilled in the art. See, e.g. (Berns et al. 2013).

In one embodiment of the invention said delivery vector comprises in addition a recombinant adeno-associated virus (AAV) vector genome or a recombinant lentivirus genome.

In one particular embodiment of the invention said delivery vector comprises in addition a recombinant AAV vector, wherein preferably said vector is a serotype of human or primate origin.

In one particular embodiment of the invention said delivery vector comprises in addition a recombinant adeno-associated virus (AAV) vector genome, wherein said vector is a human serotype vector selected from the group comprising serotypes 1, 2, 3, 4, 5, 6, 7, 8, 9, 10, rh10, 11, 12, 13, 14, serpentine AAV, ancestral AAV, or AAV capsid mutants derived thereof, preferably but not exclusively of AAV serotype 1 or 2.

In one particular embodiment of the invention said delivery vector is a single stranded AAV vector or a self-complimentary (or dimeric) duplex vector.

In one particular embodiment of the invention said delivery vector is a delivery vector as described above, wherein the DNA sequence encoding a PDGFR-alpha-derived peptide or fragment as defined herein is operatively linked to expression control elements comprising a promoter and/or enhancer that produces sufficient expression of the gene product of interest to obtain a therapeutic effect.

For example, the encoding nucleic acid may be operably associated with expression control elements, such as transcription/translation control signals, origins of replication, polyadenylation signals, and internal ribosome entry sites (IRES), promoters, enhancers, and the like. It will further be appreciated that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced. Promoter/enhancer elements that are functional in the target cell or subject to be treated are most preferred. Mammalian promoter/enhancer elements are also preferred. The promoter/enhancer element may express the transgene constitutively or inducibly.

Exemplary constitutive promoters include, but are not limited to a Beta-actin promoter, a cytomegalovirus promoter, a cytomegalovirus-enhancer/chicken beta-actin hybrid promoter, and a Rous sarcoma virus promoter. Inducible expression control elements are generally employed in those applications in which it is desirable to provide regulation over expression of the heterologous nucleic acid sequence(s). Inducible promoters/enhancer elements for gene delivery include neuron-specific, brain-specific, muscle specific (including cardiac, skeletal and/or smooth muscle), liver specific, bone marrow specific, pancreatic specific, spleen specific, and lung specific promoter/enhancer elements.

Other inducible promoter/enhancer elements include drug-inducible, hormone-inducible and metal-inducible elements, and other promoters regulated by exogenously supplied compounds, including without limitation, the zinc-inducible metallothionein (MT) promoter; the dexamethasone (Dex)—inducible mouse mammary tumor virus (MMTV) promoter; the T7 polymerase promoter system (see WO 98/10088); the ecdysone-inducible insect promoter (No et al, 1996); the tetracycline-repressible system (Gossen and Bujard, 1992); the tetracycline-inducible system (Gossen et al., 1995); see also (Harvey et al., 1998); the RU486-inducible system (Wang, DeMayo et al., 1997); (Wang, Xu et al., 1997); and the rapamycin-inducible system (Magari et al., 1997).

In a particular embodiment of the invention the promoter and/or enhancer is selected from the group comprising constitutively active promoters e.g. CMV (cytomegalovirus immediate-early gene enhancer/promoter)- or CBA promoter (chicken beta actin promoter and human cytomegalovirus IE gene enhancer), or inducible promoters comprising Gene Switch, tet-operon derived promoter, preferably but not exclusively of human origin.

In a particular embodiment of the invention said delivery vector further comprises a posttranscriptional regulatory element, preferably the woodchuck-hepatitis-virus-posttranscriptional-regulatory element. Other possible posttranscriptional regulatory elements are known to a person skilled in the art.

Subject of the present invention is furthermore a recombinant gene therapy vector comprising the foreign, therapeutic coding sequence, which is flanked by genetic elements for its expression and by virus-specific cis elements for its replication, genome packaging, genomic integration etc. The said virus genome is encapsidated as virus particle consisting of virus-specific proteins as in the case of AAV. In the case of lentivirus vectors the viral genome and virus-specific proteins, like reverse transcriptase and others are encapsidated into lentivirus capsids. These are enveloped by a lipid bilayer into which virus-specific proteins are embedded. Liposomes comprise the above described nucleotide sequences or entire DNA backbones including all regulatory elements of the gene therapy-, or delivery vector.

Examples of liposomes include DSPC (1,2-distearoyl-sn-glycero-3-phosphocholine, cholesterol, DSPE-PEG2000 (1,2-distearoyl-sn-glycero-3-phosphoethanol-amine-N-[amino(polyethylene glycol)-2000], or DSPE-PEG2000-mal (1,2-distearoyl-sn-glycero-3-phosphoethanol-amine-N-[maleimide(polyethylene glycol)-2000] or variants comprising sphingomyelin/cholesterol and phosphatidic acid.

In one particular embodiment of the invention said delivery vector comprises in addition a recombinant adeno-associated virus (AAV) vector genome and said recombinant AAV (rAAV) vector genome is encapsidated in an AAV capsid.

Adeno-associated viruses (AAV) have been developed as nucleic acid delivery vectors. For a review, see (Muzyczka, 1992). AAV are helper-dependent parvoviruses requiring a helper virus, typically adenovirus or herpesvirus for productive replication. AAV represent a growing family of currently 14 naturally occurring serotypes of human or primate origin. AAVs of other mammalian species, or of avian or insect origin have been described (see Berns et al., 2013). The AAVs have small icosahedral capsids, 18-26 nanometers in diameter and contain a single-stranded DNA genome of 4-5 kilobases in length. AAV encapsidates both AAV DNA strands, either the sense or antisense DNA strand is incorporated into one virion. The AAV genome carries two major open reading frames encoding the genes rep and cap. Rep encodes a family of overlapping, nonstructural, regulatory proteins. In the best-studied AAV prototype strain, AAV2, the mRNAs for Rep78 and Rep68 are transcribed from the AAV p5 promoter (Stutika et al. 2015). Rep78/68 are required for AAV transcription, AAV DNA replication, AAV integration into the host cell genome and its rescue therefrom. Rep52 and Rep40 represent N-terminally truncated versions of Rep78 and Rep68 transcribed from a separate promoter, p19 and are required for encapsidation of the newly synthesized AAV genome into preformed AAV capsids. These are formed by the three cap gene-derived proteins, VP1, VP2, and VP3. The cap ORF also encodes AAP, an assembly-enhancing protein that does not form part of the capsid. The AAV ORFs are flanked by inverted terminal repeat sequences (ITRs) at either end of the genome. These vary in length between AAV serotypes, in AAV2 these comprise around 145 bp, the first 125 bp thereof are capable of forming Y- or T-shaped duplex structures. The ITRs represent the minimal AAV sequences required in cis for DNA replication, packaging, genomic integration and rescue. Only these have to be retained in an AAV vector to ensure DNA replication and packaging of the AAV vector genome. Foreign genes flanked by AAV-ITRs will be replicated and packaged into AAV capsids provided the AAV genes rep and cap are expressed in trans in the chosen packaging cell (Muzyczka, 1992).

AAV are among the few viruses that can persist over months and years in non-dividing cells in vivo, including neurons, muscle, liver, heart and others. Wildtype AAV2 has been shown to integrate its genome into the host cell genome in a Rep78/68-dependent manner, with a preference for chromosomal loci with DNA sequence homology to the so-called Rep-binding site which forms part of the AAV-ITRs (Hüser et al., 2014). In contrast, AAV vectors mostly persist as nuclear episomes. Devoid of the AAV genes rep and cap AAV vectors rarely integrate at all, and if so without genomic preference (Hüser et al., 2014). Nonetheless long-term AAV persistence has been shown in non-dividing, postmitotic cells.

Generally, a recombinant AAV vector (rAAV) genome will only retain the inverted terminal repeat (ITR) sequence(s) so as to maximize the size of the transgene that can be efficiently packaged by the vector. The structural- and non-structural protein-coding sequences may be provided in trans, e.g., from a vector, such as a plasmid, by stably integrating the respective genes into a packaging cell, or in a recombinant helper virus such as HSV or baculovirus, as reviewed in (Mietzsch, Grasse et al., 2014). Typically, the rAAV vector genome comprises at least one AAV terminal repeat, more typically two AAV terminal repeats, which generally will be at the 5' and 3' ends of the heterologous nucleotide sequence(s). The AAV ITR may be from any AAV including serotypes 1-14. Since AAV2-derived ITRs can be cross-packaged into virtually any AAV serotype capsids, AAV2 ITRs combined with AAV2 rep are mostly employed. The AAV terminal repeats need not maintain the wild-type terminal repeat sequence (e.g., a wild-type sequence may be altered by insertion, deletion, truncation or missense mutations), as long as the terminal repeat mediates the desired functions, e.g., replication, virus packaging, integration, and/or provirus rescue, and the like. The rAAV vector genome is generally between 80% to about 105% of the size of the wild-type genome and comprises an appropriate packaging signal as part of the AAV-ITR. To facilitate packaging into an AAV capsid, the entire vector genome is preferably below 5.2 kb, more preferably up to 4.8 kb in size to facilitate packaging of the recombinant genome into the AAV capsid. So-called dimeric or self-complementary AAV vectors (dsAAV) were developed that package double-stranded instead of single-stranded AAV genomes (McCarty et al., 2001). These lead to enhanced AAV gene expression, however at the price of reduced transgene capacity. Only up to 2 kb of foreign genes can be packaged, which is enough for small genes or cDNAs.

Any suitable method known in the art can be used to produce AAV vectors expressing the nucleic acids of this invention. AAV vector stocks can be produced by co-transfection of plasmids for the ITR-flanked AAV vector genome expressing the transgene together with an AAV rep/cap expressing plasmid of the desired serotype and adenovirus-derived helper genes for AAV replication (Grimm et al., 2003; Xiao et al., 1998). AAV vectors can also be produced in packaging cell lines of mammalian or insect origin and/or in combination with recombinant helper viruses, such as adenovirus, herpes simplex virus (HSV), another member of the herpesvirus family, or baculovirus, as reviewed and discussed in (Mietzsch, Grasse et al., 2014).

Another embodiment of the present invention is a method of delivering a nucleic acid to a cell of the, comprising contacting the cell with the delivery vector or recombinant virus particle as described above under conditions sufficient for the DNA sequence to be introduced into the cell. The delivery vectors of the present invention provide a means for delivering nucleic acid sequences into cells of a host to be treated. The delivery vectors may be employed to transfer a nucleotide sequence of interest to a cell in vitro, e.g., to produce a polypeptide in vitro or for ex vivo gene therapy. The vectors are additionally useful in a method of delivering a nucleotide sequence to a subject in need thereof. In this manner, the polypeptide may thus be produced in vivo in the subject. The subject may be in need of the peptide because the production of the polypeptide in the subject may impart some therapeutic effect, as a method of treatment or otherwise.

In one particular embodiment of the method of delivering a nucleic acid to a cell so that the PDGFR-alpha-derived peptide is produced and released from the cell.

In one particular embodiment of the method of delivering a nucleic acid to a cell of host, wherein the method comprises contacting the cell with the recombinant virus particle or liposome as described above under conditions sufficient for the DNA sequence to be introduced into the cell. Conditions sufficient for the DNA sequence to be introduced into the cell comprise the contacting of the AAV capsid to host cell surface receptors and co-receptors. AAV1 capsids bind to 2-3 sialic acid linked to N-acetylgalactosamine, followed by 1-4-linked N-acetylglucosamine, whereas AAV2 capsids bind to heparin sulfate proteoglycan particularly 6-O- and N-sulfated heparins on the cell surface (Mietzsch, Broecker et al., 2014). AAV coreceptors include FGFR-1, Integrin aVb5, hepatocyte growth factor receptor (c-met) and a recently identified, universal AAV receptor, AAVR necessary for transduction with AAV1, AAV2 and others irrespective of the presence of specific glycans (Pillay et al., 2016). AAVR directly binds to AAV particles and helps trafficking to the trans-Golgi network. In any case AAV vectors are expressed in the cell nucleus.

One embodiment of the invention is a delivery vector or recombinant virus particle or liposome as described above for use as medicament.

One embodiment of the invention is a delivery vector or recombinant virus particle or liposome as described above for use the preparation of a medicament.

One embodiment of the invention is a method of treating a diseased subject in need of therapy by administering a delivery vector or recombinant virus particle or liposome as described above.

The delivery of peptides is known in the art as can be derived from standard textbooks such as "Peptide and Protein Delivery", AP, Chris van der Walle (Ed.). $1^{st}$ edition 2011.

Subject of the present invention is an anti-PDGFR-alpha antibody or a PDGFR-alpha antibody fragment or anti-PDGFR-alpha non-Ig scaffold binding to the HCMV binding region of PDGFR-alpha SEQ ID No. 4.

Subject of the present invention is an anti-PDGFR-alpha antibody or a PDGFR-alpha antibody fragment or anti-PDGFR-alpha non-Ig scaffold binding to the HCMV binding region of PDGFR-alpha SEQ ID No. 4 and inhibiting the binding of HCMV to PDGFR-alpha, wherein the inhibition of binding of HCMV to PDGFR-alpha is determined as follows:

Infectious cell free HCMV preparations (corresponding to a multiplicity of infection of 1) are pre-incubated with PDGFR-alpha-Fc chimera in absence or presence of the anti-PDGFR-alpha antibody or a PDGFR-alpha antibody fragment or anti-PDGFR-alpha non-Ig scaffold (at variable concentrations) for 2 h at 37° C. The pre-incubated mixture of HCMV, PDGFR-alpha-Fc chimera and anti-PDGFR-alpha antibody or a PDGFR-alpha antibody fragment or anti-PDGFR-alpha non-Ig scaffold is added to human primary fibroblasts at 0° C. Cells are incubated with the mixture for 2 h at 0° C. The mixture of HCMV, PDGFR-alpha-Fc chimera and anti-PDGFR-alpha antibody or a PDGFR-alpha antibody fragment or anti-PDGFR-alpha non-Ig scaffold is then removed and replaced with fixation solution (80% acetone) at ambient temperature. After 5 min, acetone is replaced with phosphate buffered solution (PBS) and washed three times with PBS. Bound PDGFR-alpha is detected by immunofluorescence using fluorescence-labeled anti-human-IgG-Fc antibodies. The $EC_{50}$ is determined as the concentration of the anti-PDGFR-alpha antibody or a PDGFR-alpha antibody fragment or anti-PDGFR-alpha non-Ig scaffold (given in μg/ml) that reduces the relative fluorescence units per HCMV particle by 50% as compared to irrelevant control antibodies and wherein antibodies are regarded effective if the $EC_{50}$ in the assay described above is lower than 5 μg/ml.

Subject matter of the present invention is also an anti-PDGFR-alpha antibody or a PDGFR-alpha antibody fragment or anti-PDGFR-alpha non-Ig scaffold according to the present invention that is inhibiting HCMV entry.

Subject matter of the present invention is also an anti-PDGFR-alpha antibody or a PDGFR-alpha antibody fragment or anti-PDGFR-alpha non-Ig scaffold according to the present invention for inhibiting HCMV entry for use in a method of treatment in a subject that has been infected by HCMV or for use in a method of prophylaxis of HCMV infection in a subject that has not yet been infected by HCMV.

Subject matter of the present invention is an anti-PDGFR-alpha antibody or a PDGFR-alpha antibody fragment or anti-PDGFR-alpha non-Ig scaffold according to the present invention for inhibiting HCMV entry for use in a method of treatment in a subject that has been infected by HCMV or for prophylaxis of HCMV infection in a subject that has not yet been infected by HCMV, wherein said peptide is administered, and wherein said anti-PDGFR-alpha antibody or a PDGFR-alpha antibody fragment or anti-PDGFR-alpha non-Ig scaffold is administered to a pregnant woman who is infected by HCMV, or a congenitally HCMV-infected child, or a bone marrow transplant recipient infected with HCMV, or a solid organ transplant recipients infected with HCMV.

In one aspect of the invention said anti-PDGFR-alpha antibody or a PDGFR-alpha antibody fragment or anti-PDGFR-alpha non-Ig scaffold is monospecific. "Monospecific" means that said antibody or antibody fragment or scaffold binds to one specific region encompassing preferably at least 4, or at least 5 amino acids within the target.

An antibody according to the present invention is a protein including one or more polypeptides substantially encoded by immunoglobulin genes that specifically binds an antigen. The recognized immunoglobulin genes include the kappa, lambda, alpha (IgA), gamma ($IgG_1$, $IgG_2$, $IgG_3$, $IgG_4$), delta (IgD), epsilon (IgE) and mu (IgM) constant region genes, as well as the myriad immunoglobulin variable region genes. Full-length immunoglobulin light chains are generally about 25 Kd or 214 amino acids in length. Full-length immunoglobulin heavy chains are generally about 50 Kd or 446 amino acid in length. Light chains are encoded by a variable region gene at the $NH_2$-terminus (about 110 amino acids in length) and a kappa or lambda constant region gene at the COOH-terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and $(Fab')_2$, as well as bifunctional hybrid antibodies and single chains (e.g., Lanzavecchia et al., Eur. J. Immunol. 17:105, 1987; Huston et al., Proc. Natl. Acad. Sci. U.S.A., 85:5879-5883, 1988; Bird et al., Science 242:423-426, 1988; Hood et al., Immunology, Benjamin, N.Y., 2nd ed., 1984; Hunkapiller and Hood, Nature 323:15-16, 1986).

An immunoglobulin light or heavy chain variable region includes a framework region interrupted by three hypervariable regions, also called complementarity determining regions (CDR's) (see, Sequences of Proteins of Immunological Interest, E. Kabat et al., U.S. Department of Health and Human Services, 1983). As noted above, the CDRs are primarily responsible for binding to an epitope of an antigen. An immune complex is an antibody, such as a monoclonal antibody, chimeric antibody, humanized antibody or human antibody, or functional antibody fragment, specifically bound to the antigen.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see U.S. Pat. No. 5,807,715. A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions, which have substantially no effect on antigen binding or other immunoglobulin functions. Exemplary conservative substitutions are those such as GLY, ALA; VAL, ILE, LEU; ASP, GLU; ASN, GLN; SER, THR; LYS, ARG; AND PHE, TYR. Humanized immunoglobulins can be constructed by means of genetic engineering (e.g., see U.S. Pat. No. 5,585,089). A human antibody is an antibody wherein the light and heavy chain genes are of human origin. Human antibodies can be generated using methods known in the art. Human antibodies can be produced by immortalizing a human B cell secreting the antibody of interest. Immortalization can be accomplished, for example, by EBV infection or by fusing a human B cell with a myeloma or hybridoma cell to produce a trioma cell. Human antibodies can also be produced by phage display methods (see, e.g., Dower et al., PCT Publication No. WO91/17271; McCafferty et al., PCT Publication No. WO92/001047; and Winter, PCT Publication No. WO92/20791), or selected from a human combinatorial monoclonal antibody library (see the Morphosys website). Human antibodies can also be prepared by using transgenic animals carrying a human immunoglobulin gene (for example, see Lonberg et al., PCT Publication No. WO93/12227; and Kucherlapati, PCT Publication No. WO91/10741).

In a preferred embodiment of the invention, the antibody format is selected from the group comprising Fv fragment, scFv fragment, Fab fragment, scFab fragment, (Fab)$_2$ fragment and scFv-Fc-fusion protein. In another preferred embodiment of the invention, the antibody format is selected from the group comprising scFab fragment, Fab fragment, scFv fragment and bioavailability optimized conjugates thereof, such as PEGylated fragments.

Non-Ig scaffolds may be protein scaffolds and may be used as antibody mimics as they are capable to bind to ligands or antigenes. Non-Ig scaffolds may be selected from the group comprising tetranectin-based non-Ig scaffolds (e.g. described in US 2010/0028995), fibronectin scaffolds (e.g. described in EP 1266 025; lipocalin-based scaffolds ((e.g. described in WO 2011/154420); ubiquitin scaffolds (e.g. described in WO 2011/073214), transferring scaffolds (e.g. described in US 2004/0023334), protein A scaffolds (e.g. described in EP 2231860), ankyrin repeat based scaffolds (e.g. described in WO 2010/060748), microproteins, preferably microproteins forming a cystine knot) scaffolds (e.g. described in EP 2314308), Fyn SH3 domain based scaffolds (e.g. described in WO 2011/023685) EGFR-A-domain based scaffolds (e.g. described in WO 2005/040229) and Kunitz domain based scaffolds (e.g. described in EP 1941867).

The anti-PDGFR-alpha antibody or a PDGFR-alpha antibody fragment or anti-PDGFR-alpha non-Ig scaffold according to the present invention exhibits an affinity towards human PDGFR-alpha in such that affinity constant is greater than $10^{-7}$ M, preferred $10^{-8}$ M, more preferred affinity is greater than $10^{-9}$ M, most preferred higher than $10^{-10}$ M. A person skilled in the art knows that it may be considered to compensate lower affinity by applying a higher dose of compounds and this measure would not lead out-of-the-scope of the invention. The affinity constants may be determined according to the method as described previously (40).

Subject of the present invention are also pharmaceutical formulations comprising a soluble PDGFR-alpha-Fc chimera or a PDGFR-alpha derived peptide or an anti-PDGFR-alpha antibody or a PDGFR-alpha antibody fragment or anti-PDGFR-alpha non-Ig scaffold.

Subject matter of the present invention encompass also methods for treatment of a subject that has been infected by HCMV or for prophylaxis of HCMV infection in a subject that has not yet been infected by HCMV, wherein a soluble PDGFR-alpha-Fc chimera or a PDGFR-alpha derived peptide or an anti-PDGFR-alpha antibody or a PDGFR-alpha antibody fragment or anti-PDGFR-alpha non-Ig scaffold is administered to a subject in need thereof.

The compounds of the present invention exhibit certain advantages, all of them, in particular peptide and fusion protein and binder (antibody), are effective against various HCMV strains.

The compounds of the present invention, peptide and fusion protein and binder (antibody), can inhibit HCMV infection of various cell types. In a particular embodiment of the invention, a Fc-PDGFRα fusion protein binds to and neutralizes cell-free HCMV particles at an $EC_{50}$ of 10-50 ng/ml. Treated particles show both reduced attachment to and reduced fusion with cells. In line with this result, Fc-PDGFRα was also effective when applied post-attachment.

The compounds of the present invention are in particular potent inhibitors of HCMV entry into both fibroblasts and endothelial cells. The compounds of the present invention may lead to lesser side effects during treatment in a subject. Further, the risk of developing resistance against treatment is lower when administering the compounds of the present invention in the methods of treatment in accordance of the instant invention. When using the compounds of the present invention, the risk of interference with intracellular pathways is greatly reduced.

The compounds of the present invention are fully active at lower concentrations and are thus promising regarding the ratio of desired and adverse effects. Thus, an antiviral effect can be expected at doses that would not significantly bind and sequester the natural ligand, thus limiting unwanted effects. Thus, the compounds of the present invention can be applied even in pregnant woman.

Considering their therapeutic application, the compounds of the present invention, in particular Fc-PDGFRα and PDGFRα-derived peptides, may offer a number of advantages: (i) they are host-derived and therefore assumed to be non-immunogenic, (ii) an additive effect with the established anti-HCMV drugs can be expected due to the different modes of action; (iii) they are equally effective against infection of fibroblasts and endo-/epithelial cells and (iv) resistance conferring mutations would most likely affect the entry potential of the virus and hence reduce viral fitness.

With the above context, further subject matter of the instant invention can be derived from the consecutively numbered embodiments below:

1. Soluble PDGFR-alpha-Fc chimera for inhibiting HCMV entry for use in a method of treatment in a subject that has been infected by HCMV or for use in a method of prophylaxis of HCMV infection in a subject that has not yet been infected by HCMV, wherein said soluble PDGFR-alpha-Fc chimera comprises a PDGFR-alpha sequence selected from the group comprising:

I. SEQ ID No. 2 (amino acids 24 to amino acids 524 of SEQ ID No. 1):
QLSLPSILPNENEKVVQLNSSFSLRCFGESEVSWQYPMSEEESSDVEIRN

EENNSGLFVTVLEVSSASAAHTGLYTCYYNHTQTEENELEGRHIYIYVPD

PDVAFVPLGMTDYLVIVEDDDSAIIPCRTTDPETPVTLHNSEGVVPASYD

SRQGFNGTFTVGPYICEATVKGKKFQTIPFNVYALKATSELDLEMEALKT

VYKSGETIVVTCAVFNNEVVDLQWTYPGEVKGKGITMLEEIKVPSIKLVY

TLTVPEATVKDSGDYECAARQATREVKEMKKVTISVHEKGFIEIKPTFSQ

LEAVNLHEVKHFVVEVRAYPPPRISWLKNNLTLIENLTEITTDVEKIQEI

RYRSKLKLIRAKEEDSGHYTIVAQNEDAVKSYTFELLTQVPSSILDLVDD

HHGSTGGQTVRCTAEGTPLPDIEWMICKDIKKCNNETSWTILANNVSNII

TEIHSRDRSTVEGRVTFAKVEETIAVRCLAKNLLGAENRELKLVAPTLRS

E,

II. a sequence having 90% or more identity to SEQ ID No. 2,

III. a sequence with at least 45 amino acids that is a truncated sequence of SEQ ID No. 2 or a sequence having 90% or more identity to said truncated SEQ ID No. 2, IV. variants of sequences according to items I., II., III. with substitutions at one or more of the following positions (numbering adhered to SEQ ID. No. 1):

Ile-30, Glu-52, Ser-66, Ser-67, Asp-68, Leu-80, Ser-89, His-162, Pro-169, Asp-173, Ile-188, Val-193, Lys-194, Glu-213, Lys-304, Thr-320, His-334, Arg-340, Ile-373, Lys-378, Ala-396, Ala-401, Thr-436, Thr-440, Ile-453, Val-469, Ile-476, Ser-478, Asp-480, Ser-482, Arg-487.

2. Soluble PDGFR-alpha-Fc chimera for inhibiting HCMV entry for use in a method of treatment in a subject that has been infected by HCMV or for use in a method of prophylaxis of HCMV infection in a subject that has not yet been infected by HCMV according to embodiment 1, wherein said soluble PDGFR-alpha-Fc chimera inhibits HCMV entry.

3. Soluble PDGFR-alpha-Fc chimera for inhibiting HCMV entry for use in a method of treatment in a subject that has been infected by HCMV or for use in a method of prophylaxis of HCMV infection in a subject that has not yet been infected by HCMV according to embodiment 1 or 2, wherein said soluble PDGFR-alpha-Fc chimera has at least one of the following mutations or deletions within SEQ ID No. 2 (numbering adhered to SEQ ID. No. 1):

i. Deletion of aa 150-189, ii. Deletion of aa 150-234, iii. Deletion of aa 150-290, iv. Deletion of aa 150-524, v. Deletion of aa 24-100 and deletion of aa 150-234, vi. SEQ ID No. 2 having at least one point mutation in at least one of the protein regions as specified in the above items i., ii., iii., iv., v.

4. Soluble PDGFR-alpha-Fc chimera for inhibiting HCMV entry for use in a method of treatment in a subject that has been infected by HCMV or for use in a method of prophylaxis of HCMV infection in a subject that has not yet been infected by HCMV according to embodiment 3, wherein said soluble PDGFR-alpha-Fc chimera inhibits HCMV entry and shows reduced ability to inhibit the biological activity of PDGF-type growth factors as compared to the inhibitory effect of wild type chimeras as defined in embodiment 1.

5. Soluble PDGFR-alpha-Fc chimera for inhibiting HCMV entry for use in a method of treatment in a subject that has been infected by HCMV or for use in a method of prophylaxis of HCMV infection in a subject that has not yet been infected by HCMV according to any of embodiments 1 to 4, wherein said soluble PDGFR-alpha-Fc chimera is administered to a pregnant woman who is infected by HCMV, or a congenitally HCMV-infected child, or a bone marrow transplant recipient infected with HCMV, or a solid organ transplant recipients infected with HCMV.

6. Soluble PDGFR-alpha-Fc chimera of any of the preceding embodiments, comprising a sequence selected from the group comprising:

I. SEQ ID No. 3:
QLSLPSILPNENEKVVQLNSSFSLRCFGESEVSWQYPMSEEESSDVEIRN

EENNSGLFVTVLEVSSASAAHTGLYTCYYNHTQTEENELEGRHIYIYVPD

PDVAFVPLGMTDYLVIVEDDDSAIIPEATVKGKKFQTIPFNVYALKATSE

LDLEMEALKTVYKSGETIVVTCAVFNNEVVDLQWTYPGEVKGKGITMLEE

IKVPSIKLVYTLTVPEATVKDSGDYECAARQATREVKEMKKVTISVHEKG

FIEIKPTFSQLEAVNLHEVKHFVVEVRAYPPPRISWLKNNLTLIENLTEI

TTDVEKIQEIRYRSKLKLIRAKEEDSGHYTIVAQNEDAVKSYTFELLTQV

PSSILDLVDDHHGSTGGQTVRCTAEGTPLPDIEWMICKDIKKCNNETSWT

ILANNVSNIITEIHSRDRSTVEGRVTFAKVEETIAVRCLAKNLLGAENRE

LKLVAPTLRSE,

II. SEQ ID No. 4:
QLSLPSILPNENEKVVQLNSSFSLRCFGESEVSWQYPMSEEESSDVEIRN

EENNSGLFVTVLEVSSASAAHTGLYTCYYNHTQTEENELEGRHIYIYVPD

PDVAFVPLGMTDYLVIVEDDDSAIIPCAVFNNEVVDLQWTYPGEVKGKGI

TMLEEIKVPSIKLVYTLTVPEATVKDSGDYECAARQATREVKEMKKVTIS

VHEKGFIEIKPTFSQLEAVNLHEVKHFVVEVRAYPPPRISWLKNNLTLIE

NLTEITTDVEKIQEIRYRSKLKLIRAKEEDSGHYTIVAQNEDAVKSYTFE

LLTQVPSSILDLVDDHHGSTGGQTVRCTAEGTPLPDIEWMICKDIKKCNN

ETSWTILANNVSNIITEIHSRDRSTVEGRVTFAKVEETIAVRCLAKNLLG

AENRELKLVAPTLRSE,

III. SEQ ID No. 5:
QLSLPSILPNENEKVVQLNSSFSLRCFGESEVSWQYPMSEEESSDVEIRN

EENNSGLFVTVLEVSSASAAHTGLYTCYYNHTQTEENELEGRHIYIYVPD

PDVAFVPLGMTDYLVIVEDDDSAIIPAARQATREVKEMKKVTISVHEKGF

IEIKPTFSQLEAVNLHEVKHFVVEVRAYPPPRISWLKNNLTLIENLTEIT

TDVEKIQEIRYRSKLKLIRAKEEDSGHYTIVAQNEDAVKSYTFELLTQVP

SSILDLVDDHHGSTGGQTVRCTAEGTPLPDIEWMICKDIKKCNNETSWTI

LANNVSNIITEIHSRDRSTVEGRVTFAKVEETIAVRCLAKNLLGAENREL

KLVAPTLRSE,

IV. SEQ ID No. 6:
QLSLPSILPNENEKVVQLNSSFSLRCFGESEVSWQYPMSEEESSDVEIRN

EENNSGLFVTVLEVSSASAAHTGLYTCYYNHTQTEENELEGRHIYIYVPD

PDVAFVPLGMTDYLVIVEDDDSAIIP,

V. SEQ ID No. 7:
YYNHTQTEENELEGRHIYIYVPDPDVAFVPLGMTDYLVIVEDDDSAIIP.

7. Soluble PDGFR-alpha-Fc chimera of any of the preceding embodiments, further comprising a sequence of human Fc that is SEQ ID No. 8:

LTVAGSDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWL

-continued

NGKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVDK

SRWQQGNVFSCSVMHEALHNHYTQKSLSLSPGK.

8. PDGFR-alpha derived peptide for inhibiting HCMV entry for use in a method of treatment in a subject that has been infected by HCMV or for use in a method of prophylaxis of HCMV infection in a subject that has not yet been infected by HCMV, wherein said peptide is selected from a group comprising SEQ ID No. 9 (between 10 aa and 60 aa in length), or SEQ ID No. 10, or SEQ ID No. 11, or SEQ ID No. 12, or SEQ ID No. 13, or that consists of parts of the following sequence:

i) SEQ ID No. 9 that is
VLEVSSASAAHTGLYTCYYNHTQTEENELEGRHIYIYVPDPDVAFVPLGM
TDYLVIVEDDDSAIIPCRTTDPETPVTLHN, ii) SEQ ID No. 10:
IKVPSIKLVYTLTVPEATVKDSGDYECAARQATREVKEMK, ii) SEQ ID No. 11:
GRHIYIYVPDPDVAFVPLGMTDYLVIVEDD, iv) SEQ ID No. 12:
GRHIYIYVPDPDVAFVPLGMTDYLVIVEDDDSAIIPCRTT, v) SEQ ID No. 13:
NVYALKATSELDLEMEALKTVYKSGETIVVTCAVFNNEVV, vi) a peptide fragment of SEQ ID No. 9 or SEQ ID No. 10, or SEQ ID No. 11, or SEQ ID No. 12, or SEQ ID No. 13, any of them having at least 10 amino acids, and
vii) a variant of the above items i). to vi). that exhibits at least 80% sequence identity to the peptide having the sequence of SEQ ID No. 9, or that exhibits at least 80% sequence identity to the peptide having the sequence of SEQ ID No. 10, or that exhibits at least 80% sequence identity to the peptide having the sequence of SEQ ID No. 11, or that exhibits at least 80% sequence identity to the peptide having the sequence of SEQ ID No. 12, or that exhibits at least 80% sequence identity to the peptide having the sequence of SEQ ID No. 13 or that exhibits at least 80% sequence identity to the peptide fragments of SEQ ID No. 9, SEQ ID No. 10, SEQ ID No. 11, or SEQ ID No. 12, or SEQ ID No. 13, any of them having at least 10 amino acids.

9. PDGFR-alpha derived peptide for inhibiting HCMV entry for use in a method of treatment in a subject that has been infected by HCMV or for use in a method of prophylaxis of HCMV infection in a subject that has not yet been infected by HCMV according to embodiment 8, wherein said peptide inhibits HCMV entry.

10. Soluble PDGFR-alpha derived peptide for inhibiting HCMV entry for use in a method of treatment in a subject that has been infected by HCMV or for use in a method of prophylaxis of HCMV infection in a subject that has not yet been infected by HCMV according to any of embodiments 8 or 9, wherein said peptide is administered to a pregnant woman that is infected by HCMV or a congenitally HCMV-infected child, or a bone marrow transplant recipient infected with HCMV or at risk of HCMV infection, or a solid organ transplant recipients infected with HCMV or at risk with HCMV infection.

11. Anti-PDGFR-alpha antibody or a PDGFR-alpha antibody fragment or anti-PDGFR-alpha non-Ig scaffold binding to the HCMV binding region of PDGFR-alpha SEQ ID No. 4.

12. Anti-PDGFR-alpha antibody or a PDGFR-alpha antibody fragment or anti-PDGFR-alpha non-Ig scaffold according to embodiment 11, inhibiting the binding of HCMV to PDGFR-alpha, wherein the inhibition of the binding of HCMV to PDGFR-alpha is determined as follows:

Infectious cell free HCMV preparations (corresponding to a multiplicity of infection of 1) are pre-incubated with PDGFR-alpha-Fc chimera in absence or presence of the anti-PDGFR-alpha antibody or a PDGFR-alpha antibody fragment or anti-PDGFR-alpha non-Ig scaffold (at variable concentrations) for 2 h at 37° C., The pre-incubated mixture of HCMV, PDGFR-alpha-Fc chimera and anti-PDGFR-alpha antibody or a PDGFR-alpha antibody fragment or anti-PDGFR-alpha non-Ig scaffold is added to human primary fibroblasts at 0° C., Cells are incubated with the mixture for 2 h at 0° C., The mixture of HCMV, PDGFR-alpha-Fc chimera and anti-PDGFR-alpha antibody or a PDGFR-alpha antibody fragment or anti-PDGFR-alpha non-Ig scaffold is then removed and replaced with fixation solution (80% acetone) at ambient temperature, After 5 min, acetone is replaced with phosphate buffered solution (PBS) and washed three times with PBS, Bound PDGFR-alpha is detected by immunofluorescence using fluorescence-labeled anti-human-IgG-Fc antibodies, The EC50 is determined as the concentration of the anti-PDGFR-alpha antibody or a PDGFR-alpha antibody fragment or anti-PDGFR-alpha non-Ig scaffold (given in µg/ml) that reduces the relative fluorescence units per HCMV particle by 50% as compared to irrelevant control antibodies, and wherein antibodies are regarded effective if the $EC_{50}$ in the assay described above is lower than 5 µg/ml.

13. Anti-PDGFR-alpha antibody or a PDGFR-alpha antibody fragment or anti-PDGFR-alpha non-Ig scaffold according to embodiment 11 or 12 inhibiting HCMV entry.

14. Anti-PDGFR-alpha antibody or a PDGFR-alpha antibody fragment or anti-PDGFR-alpha non-Ig scaffold according to any of embodiments 11 to 13 for inhibiting HCMV entry for use in a method of treatment in a subject that has been infected by HCMV or for use in a method of prophylaxis of HCMV infection in a subject that has not yet been infected by HCMV.

15. Anti-PDGFR-alpha antibody or a PDGFR-alpha antibody fragment or anti-PDGFR-alpha non-Ig scaffold according to any of embodiments 11 to 14 for inhibiting HCMV entry for use in a method of treatment in a subject that has been infected by HCMV or for use in a method of prophylaxis of HCMV infection in a subject that has not yet been infected by HCMV, wherein said peptide is administered, and wherein said anti-PDGFR-alpha antibody or a PDGFR-alpha antibody fragment or anti-PDGFR-alpha non-Ig scaffold is administered to a pregnant woman who is infected by HCMV, or a congenitally HCMV-infected child, or a bone marrow transplant recipient infected with HCMV, or a solid organ transplant recipients infected with HCMV.

```
Sequence Listing
SEQ ID No. 1 (PDGFR-alpha (ISOFORM 1)):
         10         20         30         40         50
MGTSHPAFLV LGCLLTGLSL ILCQLSLPSI LPNENEKVVQ LNSSFSLRCF 60         70         80         90        100
GESEVSWQYP MSEEESSDVE IRNEENNSGL FVTVLEVSSA SAAHTGLYTC 110        120        130        140        150
YYNHTQTEEN ELEGRHIYIY VPDPDVAFVP LGMTDYLVIV EDDDSAIIPC 160        170        180        190        200
RTTDPETPVT LHNSEGVVPA SYDSRQGFNG TFTVGPYICE ATVKGKKFQT 210        220        230        240        250
IPFNVYALKA TSELDLEMEA LKTVYKSGET IVVTCAVFNN EVVDLQWTYP 260        270        280        290        300
GEVKGKGITM LEEIKVPSIK LVYTLTVPEA TVKDSGDYEC AARQATREVK 310        320        330        340        350
EMKKVTISVH EKGFIEIKPT FSQLEAVNLH EVKHFVVEVR AYPPPRISWL 360        370        380        390        400
KNNLTLIENL TEITTDVEKI QEIRYRSKLK LIRAKEEDSG HYTIVAQNED 410        420        430        440        450
AVKSYTFELL TQVPSSILDL VDDHHGSTGG QTVRCTAEGT PLPDIEWMIC 460        470        480        490        500
KDIKKCNNET SWTILANNVS NIITEIHSRD RSTVEGRVTF AKVEETIAVR 510        520        530        540        550
CLAKNLLGAE NRELKLVAPT LRSELTVAAA VLVLLVIVII SLIVLVVIWK 560        570        580        590        600
QKPRYEIRWR VIESISPDGH EYIYVDPMQL PYDSRWEFPR DGLVLGRVLG 610        620        630        640        650
SGAFGKVVEG TAYGLSRSQP VMKVAVKMLK PTARSSEKQA LMSELKIMTH 660        670        680        690        700
LGPHLNIVNL LGACTKSGPI YIITEYCFYG DLVNYLHKNR DSFLSHHPEK 710        720        730        740        750
PKKELDIFGL NPADESTRSY VILSFENNGD YMDMKQADTT QVPMLERKE 760        770        780        790        800
VSKYSDIQRS LYDRPASYKK KSMLDSEVKN LLSDDNSEGL TLLDLLSFTY 810        820        830        840        850
QVARGMEFLA SKNCVHRDLA ARNVLLAQGK IVKICDFGLA RDIMHDSNYV 860        870        880        890        900
SKGSTFLPVK WMAPESIFDN LYTTLSDVWS YGILLWEIFS LGGTPYPGMM 910        920        930        940        950
VDSTFYNKIK SGYRMAKPDH ATSEVYEIMV KCWNSEPEKR PSFYHLSEIV 960        970        980        990       1000
ENLLPGQYKK SYEKIHLDFL KSDHPAVARM RVDSDNAYIG VTYKNEEDKL 1010       1020       1030       1040       1050
KDWEGGLDEQ RLSADSGYII PLPDIDPVPE EEDLGKRNRH SSQTSEESAI 1060       1070       1080
ETGSSSSTFI KREDETIEDI DMMDDIGIDS SDLVEDSFL SEQ ID No. 2 (i.e. aa 24-aa 524 of SEQ ID No. 1):
   QLSLPSI LPNENEKVVQ LNSSFSLRCF GESEVSWQYP MSEEESSDVE IRNEENNSGL

FVTVLEVSSA SAAHTGLYTC YYNHTQTEEN ELEGRHIYIY VPDPDVAFVP

LGMTDYLVIV EDDDSAIIPC RTTDPETPVT LHNSEGVVPA SYDSRQGFNG

TFTVGPYICE ATVKGKKFQT IPFNVYALKA TSELDLEMEA LKTVYKSGET

IVVTCAVFNN EVVDLQWTYP GEVKGKGITM LEEIKVPSIK LVYTLTVPEA

TVKDSGDYEC AARQATREVK EMKKVTISVH EKGFIEIKPT FSQLEAVNLH
```

-continued

EVKHFVVEVR AYPPPRISWL KNNLTLIENL TEITTDVEKI QEIRYRSKLK

LIRAKEEDSG HYTIVAQNED AVKSYTFELL TQVPSSILDL VDDHHGSTGG

QTVRCTAEGT PLPDIEWMIC KDIKKCNNET SWTILANNVS NIITEIHSRD

RSTVEGRVTF AKVEETIAVR CLAKNLLGAE NRELKLVAPT LRSE

SEQ ID No. 3 (Deletion of IgG-like loop 2; i.e. deletion of aa 150 to aa 189 of SEQ ID No. 2):
QLSLPSILPNENEKVVQLNSSFSLRCFGESEVSWQYPMSEEESSDVEIRNEENN

SGLFVTVLEVSSASAAHTGLYTCYYNHTQTEEN ELEGRHIYIY VPDPDVAFV

PLGMTDYLVIV EDDDSAIIPEATVKGKKFQTIPFNVYALKATSELDLEMEALK

TVYKSGETIVVTCAVFNNEVVDLQWTYPGEVKGKGITMLEEIKVPSIKLVYTLT

VPEATVKDSGDYECAARQATREVKEMKKVTISVHEKGFIEIKPTFSQLEAVNLH

EVKHFVVEVRAYPPPRISWLKNNLTLIENLTEITTDVEKIQEIRYRSKLKLIRA

KEEDSGHYTIVAQNEDAVKSYTFELLTQVPSSILDLVDDHHGSTGGQTVRCTAE

GTPLPDIEWMICKDIKKCNNETSWTILANNVSNIITEIHSRDRSTVEGRVTFAK

VEETIAVRCLAKNLLGAENRELKLVAPTLRSE

SEQ ID No. 4 (Deletion of IgG-like loop 2 till loop 3; i.e. deletion of aa 150-aa 234 of SEQ ID No. 2):
QLSLPSILPNENEKVVQLNSSFSLRCFGESEVSWQYPMSEEESSDVEIRNEENN

SGLFVTVLEVSSASAAHTGLYTCYYNHTQTEENELEGRHIYIYVPDPDVAFVPL

GMTDYLVIVEDDDSAIIPCAVFNNEVVDLQWTYPGEVKGKGITMLEEIKVPSIK

LVYTLTVPEATVKDSGDYECAARQATREVKEMKKVTISVHEKGFIEIKPTFSQL

EAVNLHEVKHFVVEVRAYPPPRISWLKNNLTLIENLTEITTDVEKIQEIRYRSK

LKLIRAKEEDSGHYTIVAQNEDAVKSYTFELLTQVPSSILDLVDDHHGSTGGQT

VRCTAEGTPLPDIEWMICKDIKKCNNETSWTILANNVSNIITEIHSRDRSTVEG

RVTFAKVEETIAVRCLAKNLLGAENRELKLVAPTLRSE

SEQ ID No. 5 (Deletion of IgG-like loops 2 and 3; i.e. deletion of aa 150-aa 290 of SEQ ID No. 2):
QLSLPSILPNENEKVVQLNSSFSLRCFGESEVSWQYPMSEEESSDVEIRNEENN

SGLFVTVLEVSSASAAHTGLYTCYYNHTQTEENELEGRHIYIYVPDPDVAFVPL

GMTDYLVIVEDDDSAIIPAARQATREVKEMKKVTISVHEKGFIEIKPTFSQLEA

VNLHEVKHFVVEVRAYPPPRISWLKNNLTLIENLTEITTDVEKIQEIRYRSKLK

LIRAKEEDSGHYTIVAQNEDAVKSYTFELLTQVPSSILDLVDDHHGSTGGQTVR

CTAEGTPLPDIEWMICKDIKKCNNETSWTILANNVSNIITEIHSRDRSTVEGRV

TFAKVEETIAVRCLAKNLLGAENRELKLVAPTLRSE

SEQ ID No. 6 (Deletion of the ECD excluding Domain 1; i.e. deletion of aa 150-aa 524 of SEQ ID No. 2):
QLSLPSILPNENEKVVQLNSSFSLRCFGESEVSWQYPMSEEESSDVEIRNEENN

SGLFVTVLEVSSASAAHTGLYTCYYNHTQTEENELEGRHIYIYVPDPDVAFVPL

GMTDYLVIVEDDDSAIIP

SEQ ID No. 7 (Deletion of the ECD excluding aa 101-149; i.e. deletion of aa 24-aa 100 and deletion of aa 150-aa 234 of SEQ ID No. 2):
YYNHTQTEENELEGRHIYIYVPDPDVAFVPLGMTDYLVIVEDDDSAIIP SEQ ID No. 8:
LTVAGSDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGFYPSD

-continued

IAVEWESNGQPENNYKTTPPVLDSDGSFFLYSKLTVDKSRWQQGNVFSCSVMHE

ALHNHYTQKSLSLSPGK

SEQ ID No. 9:
VLEVSSASAAHTGLYTCYYNHTQTEENELEGRHIYIYVPDPDVAFVPLGMTDYL

VIVEDDDSAIIPCRTTDPETPVTLHN

SEQ ID No. 10:
IKVPSIKLVYTLTVPEATVKDSGDYECAARQATREVKEMK

SEQ ID No. 11:
GRHIYIYVPDPDVAFVPLGMTDYLVIVEDD

SEQ ID No. 12:
GRHIYIYVPDPDVAFVPLGMTDYLVIVEDDDSAIIPCRTT

SEQ ID No. 13:
NVYALKATSELDLEMEALKTVYKSGETIVVTCAVFNNEVV

EXAMPLES

Example 1

Cells and Viruses:

Primary human foreskin fibroblast (HFFs) were propagated in MEM (plus GlutaMaxx; Gibco) supplemented with 5% fetal calf serum (FCS), 100 µg/ml gentamycin and 0.5 ng/ml basic fibroblast growth factor. During experiments the cells were kept in maintenance medium without growth factor. Conditionally immortalized human endothelial cells (HEC-LTT, short HEC) (25, 28), were proliferated on vessels coated with 0.1% gelatin in endothelial cells growth medium (bullet kit; Lonza) with 2 µg/ml doxycycline. For experiments, the HECs were withdrawn from doxycycline for 24 hours to control the cell numbers of this otherwise fast dividing cell line. The efficiently transfectable hybrid endothelial cell line EA.hy926 (ATCC: CRL-2922; Edgell 1983) was expanded in DMEM (life technologies) plus 10% FCS.

The HCMV strains TB40/E and TB40/F were isolated from the same patient. TB40/E was propagated on endothelial cells and is highly endotheliotropic, whereas TB40/F was kept on fibroblast and is non-endotheliotropic (Sinzger 1999). AD169 (Rowe 1956 Plotkin 1975) and Towne (Plotkin 1975) are widely used HCMV strains, but lack the pentameric complex and are therefore non-endotheliotropic. VR1814 (Revello 2001), VHL/E (Waldman 1991) and Merlin (Davison 2003) represent endotheliotropic HCMV strains. TB40-BAC$_{KL7}$-UL32EGFP-UL100mCherry is an endotheliotropic descendant of TB40/E that was labelled to allow differentiation between enveloped and non-enveloped virus capsids (Sampaio 2013).

TB40-BAC4 is a highly endotheliotropic BACmid based on TB40/E (Sinzger 2008) and BAC4UL74stop is an (yet unpublished) BAC4 mutant in which M7 and K12 of pUL74 were changed to stop codons, resulting in loss of expression of pUL74 (gO). Virus stocks of TB40 variants, AD169, Towne, VHL/E and VR1814 were harvested from infected HFFs day 5 to 7 post infection (p.i.). Supernatants were cleared from cells and large cell debris by centrifugation at 2,700 g for 10 min before storage at −80° C. Cleared UL74stop supernatants were 50 fold concentrated by ultracentrifugation at 70,000 g for 70 min. The luciferase reporter virus contains a *Gaussia* expression cassette under control of the major immediate early promoter, therefore the luciferase is expressed with the same kinetics as the immediate early proteins of HCMV (10). Virus stocks of the *Gaussia* luciferase reporter virus were first cleared and then twice ultracentrifuged at 23000 g for 70 min to remove Luciferase that is secreted along with the virus particles.

Example 2

Antiviral Drugs, Chimeric Receptor Molecules and PDGFRα-Derived Peptides:

All recombinant Fc-fusion proteins used in these studies were obtained from R&D: PDGFR-alpha-Fc (6765-PR-050), PDGFRβ-Fc (385-PR-100), EGFR-Fc (344-ER-050). The 40 amino acid long peptides based on human PDGFRα isotype 1 extracellular domain were obtained from Phtdpeptides, Shanghai, China. All peptides were dissolved to a final concentration of 1 mmol/l. Depending on their physiochemical properties either water, ammonium carbonate, dimethyl sulfoxide or acetic acid were used as solvents.

Example 3

Knockdown of Protein Expression by siRNA:

For reverse transfection of siRNAs, cells were seeded at a density of 10,000 per well. As a negative control the inventors used siGenome non-targeting pool #2 (Dharmacon), as a positive control served a highly efficient IE siRNA (Hochdorfer 2016). Targets were knocked down with pools of four different siRNAs (siGenome Dharmacon). For each transfection using Lipofectamin RNAiMAX (Life Technologies) a final concentration of 50 nM was applied. 48 h post transfection HCMV TB40/E was added to the cells at a multiplicity of 0.5 to 1. Infection was allowed for 1 day before cells were fixed and stained for viral immediate early antigens.

Example 4

Inhibition of Infection:

For testing the inhibitory effect of antivirals or fusion proteins on HCMV, the respective inhibitors were diluted in MEM and mixed with infectious supernatants, the mixtures were incubated for 2 h at 37° C. before addition to the cells. For fibroblast infection the virus-inhibitor mixture was incubated on the cells for about 24 h. If endothelial cells were included in the experiment, all cells were supplied with their respective maintenance media after 2 h, and further incubated for 22 h.

Example 5

Determination of Infection Efficiencies:

Infection efficiencies were determined by immunofluorescence staining for viral proteins. For fixation and permeabilization the cells were incubated with 80% acetone for 5 min. For HCMV infected cells the immediate early proteins pUL122/123 were detected with a mouse monoclonal (clone E13, Argene) and visualized using a Cy3 conjugated goat anti-mouse secondary antibody (Jackson Immuno Research). HSV infected cultures were stained 6 h post infection for ICP0 using a mouse monoclonal (clone 11060, Santa Cruz) and goat anti-mouse AF488 (life technologies). DAPI was used to locate nuclei. Infection rates were determined by counting the number of cell nuclei positive for the respective viral protein, as well as the total number of nuclei per image. For each condition three images were evaluated.

For screening the PDGFRα peptides for their neutralizing capacity a recently developed *Gaussia*-Luciferase-Assay was utilized (10). The *Gaussia* luciferase is secreted into the cell culture supernatants, therefore it is not necessary to fix the cells and instead a sample of the *Gaussia* containing supernatant is taken and mixed with the substrate coelenterazine (PjK) at a final concentration of 0.2 µg/ml. The resulting light emission was detected at 495 nm. For all obtained values background signals were subtracted and neutralization efficiency was determined relative to the control samples which contained only virus, no peptide.

Example 6

Quantification of Adsorption and Penetration:

To distinguish between adsorption and penetration of viral particles the inventors made use of dual fluorescent HCMV TB40-BAC$_{KL7}$-UL32EGFP-UL100mCherry (Sampaio 2013). HFFs and HECs were seeded at a density of 40,000 cells per well on gelatin-coated MIDI plates. Overnight produced cell-free infectious supernatant of the fluorescent virus was pre-incubated with PDGFR-Fcs for 2 h at 37° C. Before addition of the mixture the cells were pre-incubated with MEM for 30 min. Penetration of virus particles which had been pre-incubated for 2 h with 500 ng/ml of Fc-fusion protein, was allowed for 2 h at 37° C. After fixation with acetone, the EGFP signal of pUL32-EGFP was enhanced using mouse-anti-GFP (clone 3E6, Invitrogen) and Alexa488-anti-mouse (Life Technologies). DAPI (4',6-diamidino-2-phenylindole) was added to mark the cell nuclei. The number of mCherry and EGFP positive particles which are enveloped was compared to the number of particles which were only green per cell. These EGFP-mCherry double positive particles have lost their UL100mCherry containing envelope, presumably by fusion with cellular membranes.

Example 7

Analysis of Post Adsorption Inhibitory Effects:

For the analysis of post adsorption inhibition, HFFs were seeded at a density of 40,000 per well on IBIDI plates and incubated for 1 day before infection. Infectious supernatants of TB40E which were produced within 24 hours were cleared by centrifugation. Two identical plates were treated as follows: Cells and virus dilutions were precooled on ice for 15 min before attachment of the virus was allowed on ice for 1 h. The virus containing medium was exchanged by pre-cooled MEM with or without 200 ng/ml PDGFR-alpha-Fc. After 2 h incubation of the inhibitor with the cells on ice, one plate was directly shifted to 37° C., whereas the other cells were treated with pre-warmed 50% PEG (Roche) for 30 sec. The PEG was washed off by five times washing with pre-warmed PBS. Supplied with pre-warmed MEM containing again 200 ng/ml PDGFR-alpha-Fc, the cells were then incubated at 37° C. After 2 h incubation the medium was exchanged on PEG-treated and untreated cells and infection was allowed to proceed for 24 h before infection efficiencies were assessed by immediate early staining. Efficient PEG fusion was controlled visually by detection of syncytia.

Example 8

Binding of Chimeric Receptors to HCMV Particles:

To assess the binding of Fc-Proteins to virus particles, HFFs were seeded at a density of 40,000 cells per well on IBIDI plates 1 day prior to infection. Virus preparations were pre-incubated with Fc-fusion proteins at a final concentration of 500 ng/ml for 2 h at 37° C. The virus/Fc-protein mixtures were incubated with the cells for 1.5 h on ice. Before fixation with 80% acetone, the cells were washed once with MEM. For staining of viral particles mouse hybridoma recognizing the abundant viral protein pp150 (generously provided by W. Britt, Sanchez 2000) used. As a secondary antibody goat anti-mouse Cy3 (Jackson Immuno Research was used. Visualization of bound Fc-proteins was achieved by applying anti-human Alexa488 (Invitrogen). For better orientation, cell nuclei were stained with DAPI. For quantification of PDGFR-alpha-Fc binding to HCMV particles, the grey values of 100 particles per condition were quantified using AxioVision Software (Zeiss).

Example 9

Knockdown of PDGFR-Alpha Prevents HCMV Infection of Fibroblasts but not of Endothelial Cells Two cellular growth factor receptor molecules, PDGFR-alpha and EGFR have been reported to promote HCMV infection in fibroblasts (33, 39). However, only fibroblast-restricted virus strains lacking the pentameric complex were used in those analyses, and in subsequent studies their relevance for HCMV infection was questioned (21, 35). As we aimed at exploring the potential of these molecules to serve as a basis for the development of HCMV entry inhibitors, the first step was to confirm their contribution to HCMV infection. To address the diverse entry pathways of HCMV the inventors applied a virus strain expressing both gH/gL complexes on two model cell types representing the restricted tropism (fibroblasts) or the extended tropism (endothelial cells).

Using an siRNA approach, the respective growth receptor was knocked down 2 days before infection with HCMV strain TB40/E at an MOI of 1. Cells treated with non-targeting siRNAs served as negative controls while cells in which viral IE RNAs were knocked down served as positive controls. One day after infection, cell cultures were fixed, viral IE antigens were immunostained, and the fraction of IE-antigen-positive cells was determined. In each of three experiments, the relative infection efficiency as compared to the non-targeting control was determined. As expected, knockdown of viral IE RNAs partially reduced the infection efficiency. Knockdown of PDGFR-alpha almost completed prevented HCMV infection of fibroblasts whereas it had no inhibitory effect in endothelial cells (FIG. 1). Knockdown of EGFR did not reduce infection efficiencies in any of the cell types.

In line with these results PDGFR-alpha was only found on the surface of fibroblasts but not on endothelial cells in immunofluorescence stainings, and surface expression in fibroblasts was suppressed to levels below the detection limit when they were treated with the respective siRNAs (data not shown).

In conclusion, of the two growth factor receptor molecules that had previously been reported to promote HCMV entry, only the contribution of PDGFR-alpha was confirmed in the present experimental setting.

Example 10

Pretreatment of HCMV with a Soluble PDGFR-Fc Chimera Inhibits Infection of Fibroblasts and Endothelial Cells The strong dependence of HCMV infection on expression of PDGFR-alpha suggested that viral particles interacted physically with this cellular growth factor receptor during the entry process in HFFs. The instant inventors found that pre-treatment of viral particles with soluble forms of this cellular molecule might block the respective interaction sites of the surface of HCMV virions and hence inhibit infection. To test this, the inventors pre-incubated cell free preparations of HCMV strain TB40/E with variable concentrations of soluble PDGFR-alpha-Fc chimeras for 2 h before adding them to HFFs and HECs. After 2 h the virus was removed and replaced with the appropriate cell culture medium for an overnight incubation. Cultures were then fixed, and the fraction of infected cells was determined by indirect immunofluorescence staining of viral IE antigens. Actually, PDGFR-alpha-Fc inhibited infection of HFFs in a dose dependent manner with an $EC_{50}$ of about 10-20 ng/ml and a complete abrogation of infection at 200 ng/ml (FIG. 2A). Unexpectedly, infection of HECs was also inhibited albeit slightly higher concentrations were needed ($EC_{50}$=20-50 ng/ml) and reduction was incomplete (FIG. 2B).

To address the possibility that the effect is rather due to the Fc part of the chimeric molecule than to the growth receptor part, the inventors compared PDGFR-alpha-Fc with EGFR-Fc and PDGFR-β-Fc regarding their inhibitory potential on HCMV infection. Cell free preparations of TB40/E were pre-incubated with increasing concentrations of the various Fc chimeras for 2 h. HFFs were then incubated with the mixtures for 2 h followed by a medium exchange and an overnight incubation. Evaluation of the infection rates by immunofluorescence staining of viral IE antigen showed that only PDGFR-alpha-Fc blocked infection in a dose dependent fashion, whereas neither PDGFR-beta-Fc nor EGFR-Fc had an effect (FIG. 3A). As the Fc-part is identical with all three molecules, the inhibitory effect is obviously due to the growth factor receptor part of the PDGFR-alpha-Fc chimera.

Next, it was tested whether soluble PDGFR-alpha-Fc would inhibit not only strain TB40/E but also other strains of HCMV. The inventors prepared cell free stocks of five HCMV strains (AD169, Towne, Merlin, VR1814, VHL/E) that represent the envelope glycoprotein variants described for HCMV (32), pre-incubated them with PDGFR-alpha-Fc at a concentration (250 ng/ml) that was sufficient for complete inhibition of strain TB40/E in the previous dose response experiment. In addition, TB40/F was included, a variant of TB40/E that lacks the pentameric gH/gL complex. After pre-incubation of the various HCMV preparations with PDGFR-alpha-Fc for 2 h, the mixture was added to HFFs in a 96-well format for 2 h and then replaced with medium. After an overnight incubation, the fraction of infected cells was determined by immunofluorescence staining of viral immediate early antigen. All strains were strongly inhibited by pretreatment with the soluble receptor, and with the exception of strain VR1814 (residual infection rate <2%) the reduction was complete (FIG. 3B). Remarkably, susceptibility to inhibition by the PDGFR-alpha-Fc was independent of whether the strain contains the pentameric glycoprotein complex or not.

Finally, to test whether this inhibitory effect was specific for HCMV the inventors repeated the experiment and included another herpes virus, HSV-1 strain F. While the inhibitory effect on HCMV was always reproduced, HSV infection was not affected by PFGFR-alpha (data not shown), indicating that the effect is specific for HCMV.

Example 11

Inhibition of HCMV Infection by PDGFR-Alpha Occurs at the Level of Viral Entry

Figure 4:
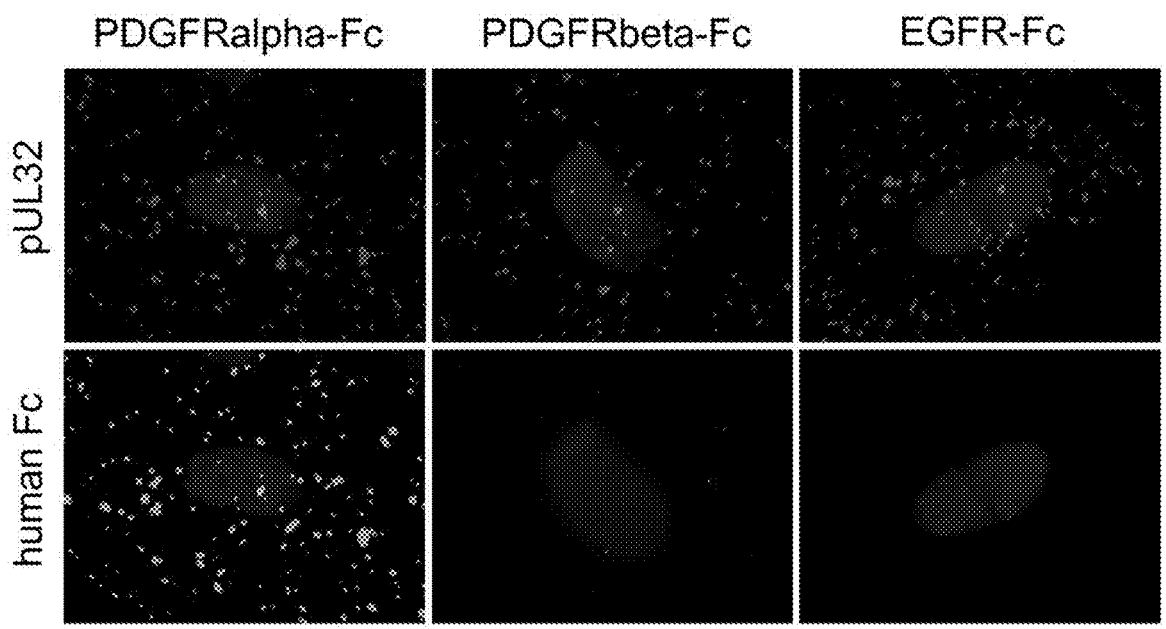

The findings that removal of PDGFRα from the cell surface as well as pre-treatment of virus with soluble PDGFRα abrogated infection suggest interference with viral entry as the mode of action. It seemed therefore most likely that PDGFR-alpha-Fc binds directly to HCMV virus particles. The inventors tested this by staining of adsorbed virus particles with the Fc-fusion proteins. HCMV particles were pre-incubated with PDGFR-alpha-Fc, PDGFR-beta-Fc or EGFR-Fc for 90 min at 37° C. before the virus was attached to the cells for 90 min on ice. Virus particles were stained for the capsid protein pp150 and bound Fc-fusion proteins. The anti-human antibody visualized only those particles that were pre-treated with PDGFR-alpha-Fc, indicating that only this growth factor receptor-chimera binds to the virus (FIG. 4).

Figure 5:
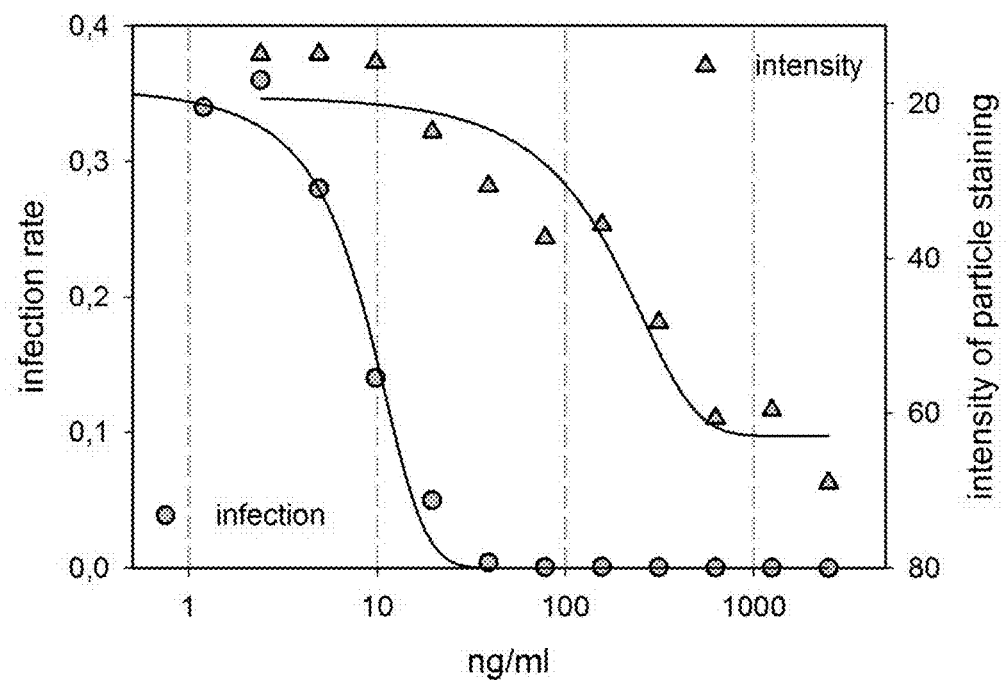

The inventors analyzed the mode of inhibition by PDGFR-alpha-Fc. For this, the binding of different concentrations of the fusion protein was quantified by assessing the particle intensities after staining with anti-human antibody (FIG. 5). The resulting $EC_{50}$ of binding to HCMV particles was 108 ng/ml, 10 fold higher than the $EC_{50}$ for inhibition of HCMV, indicating that PDGFR-alpha-Fc does not only sterically hinder entry of HCMV particles, but also inactivates them. (FIGS. 4 and 5).

Figure 6:
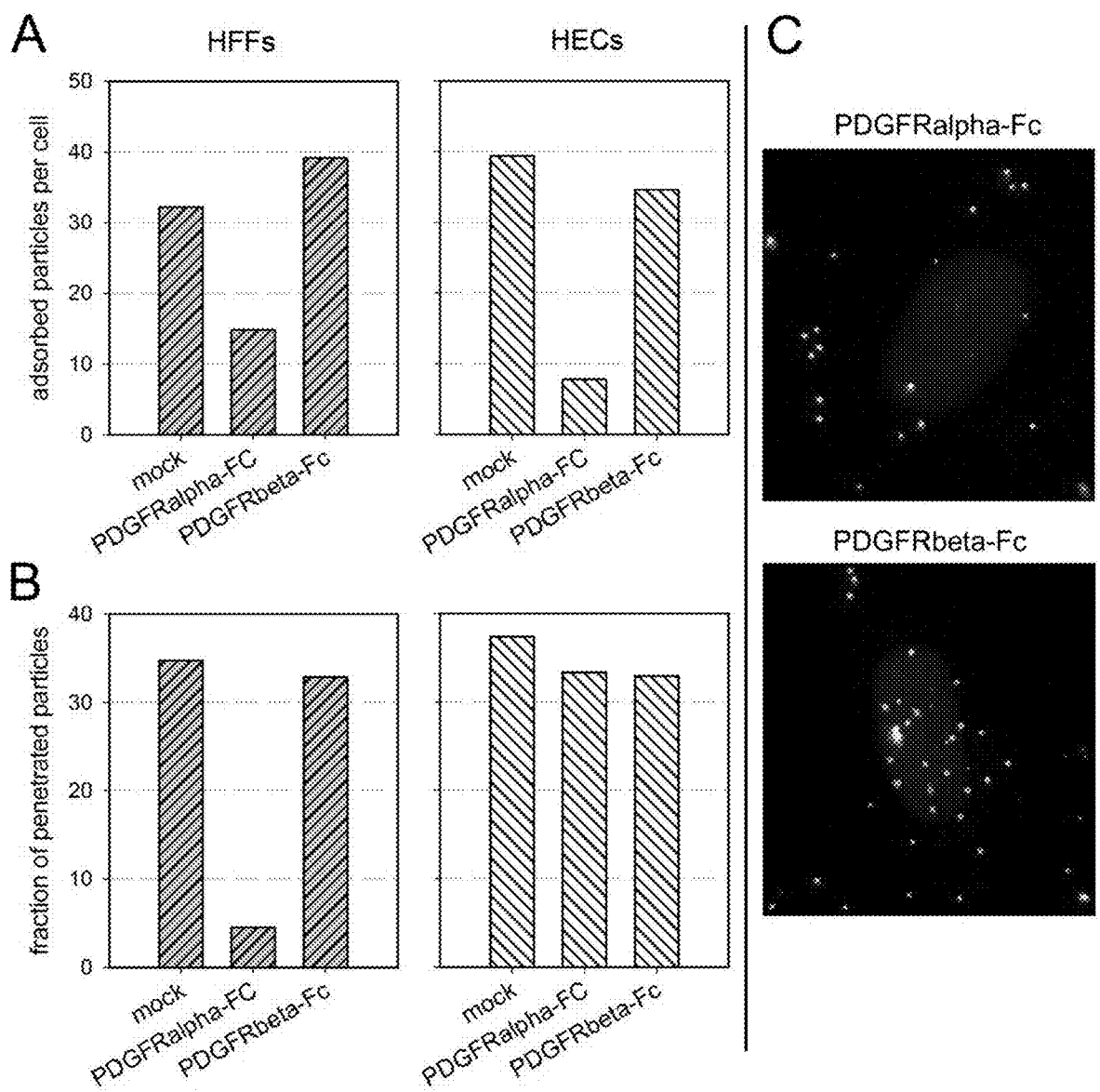

To further investigate, which of the initial steps of infection are blocked, the inventors performed a series of experiments that allowed discriminating between adsorption and penetration. They used the dual fluorescent virus TB40-$BAC_{KL7}$-UL32EGFP-UL100mCherry (Sampaio 2013) as it allows to discriminate between enveloped (EGFP-positive and mCherry positive) and non-enveloped particles (only EGFP positive). They compared adsorption and penetration of untreated particles with particles pre-incubated with 100 ng/ml PDGFR-alpha or beta by counting the number of enveloped versus naked particles. On both cell types HFFs and HECs, adsorption of PDGFR-alpha-treated particles was reduced (50% on HFFs and 75% on HECs), whereas penetration was affected only in fibroblasts (FIG. 6). PDGFR-alpha-treated particles penetrated HFFs 75% less efficient, indicating that soluble PDGFR-alpha-Fc generally hinders HCMV attachment and specifically inhibits penetration of fibroblasts. Several experiments in which the inventors tested different time points and concentrations gave similar results.

As the inhibition of penetration indicated that virions treated with PDGFR-alpha-Fc are defective for fusion of their envelope with the cellular plasma membrane, the inventors tested whether the chemical fusogen PEG was able to rescue this post-attachment inhibition by PDGFR-alpha-Fc. HCMV virus particles were adsorbed to HFFs for 1 h on ice. The virus containing medium was then exchanged by medium containing PDGFR-alpha-Fc at a concentration of 200 ng/ml. Inhibition of pre-adsorbed virus was allowed for 2 more hours on ice, before the cells were either directly shifted to 37° C. to allow entry or first treated with pre-warmed PEG for 30 sec. The PEG was washed off before the addition of PDGFR-alpha-Fc containing medium. After 2 h of incubation at 37° C. the cells were supplied with fresh medium without inhibitor and further incubated overnight. After 24 h the cells were fixed and stained for the viral immediate early antigens.

Figure 7:
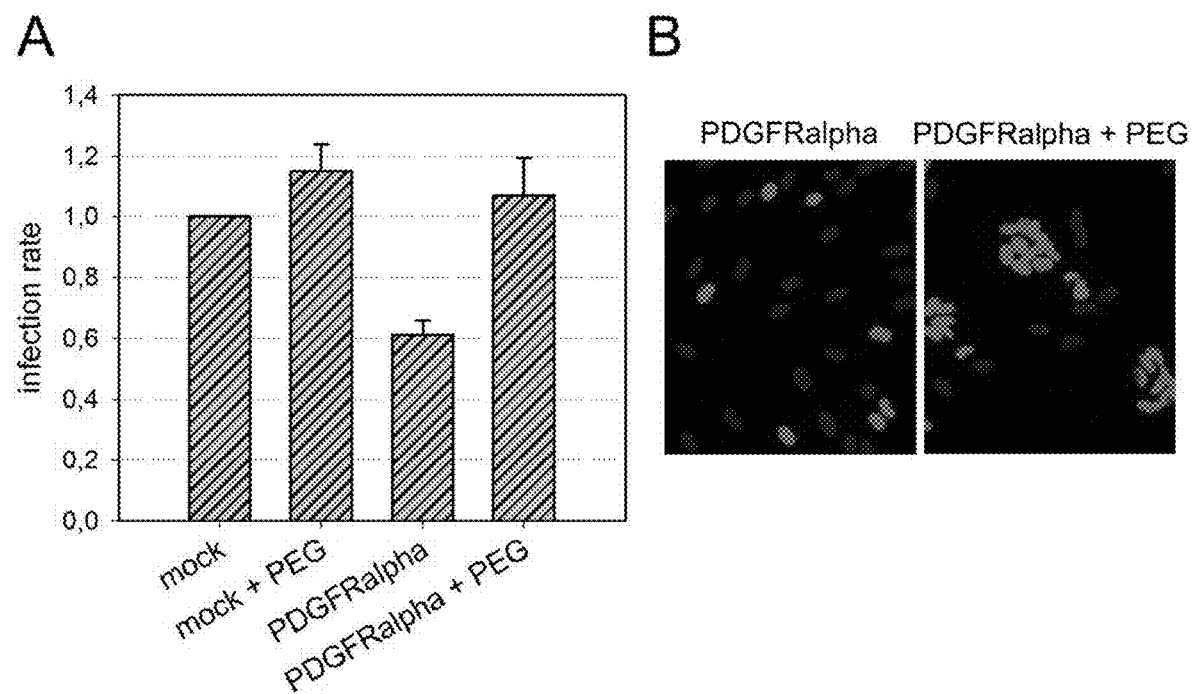

PDGFR-alpha-Fc reduced infectivity of already adsorbed viruses to 50% (FIG. 7). This inhibition was completely rescued by addition of PEG, whereas PEG did not increase the infection of untreated control virus, indicating that PDGFR-alpha-Fc inhibits the fusion step of HCMV entry.

Figure 8:
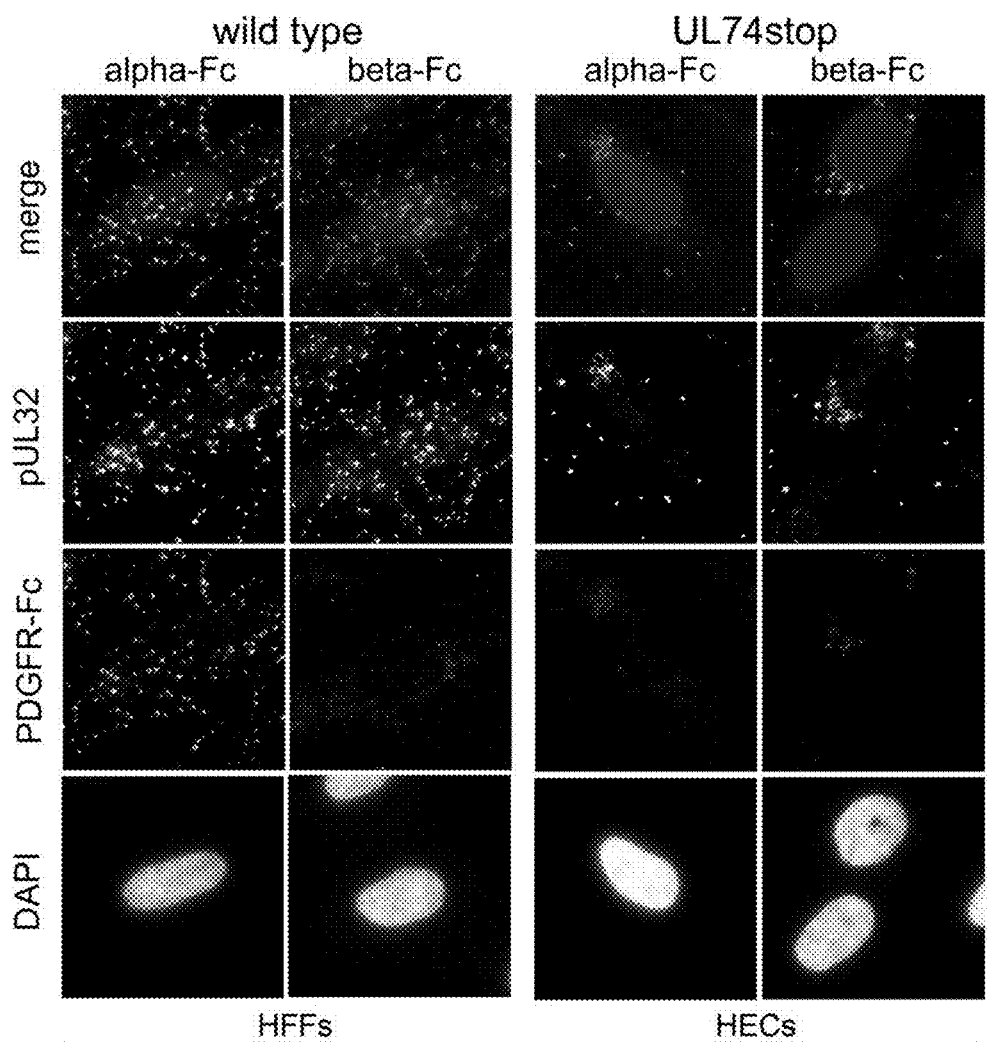
Figure 8:
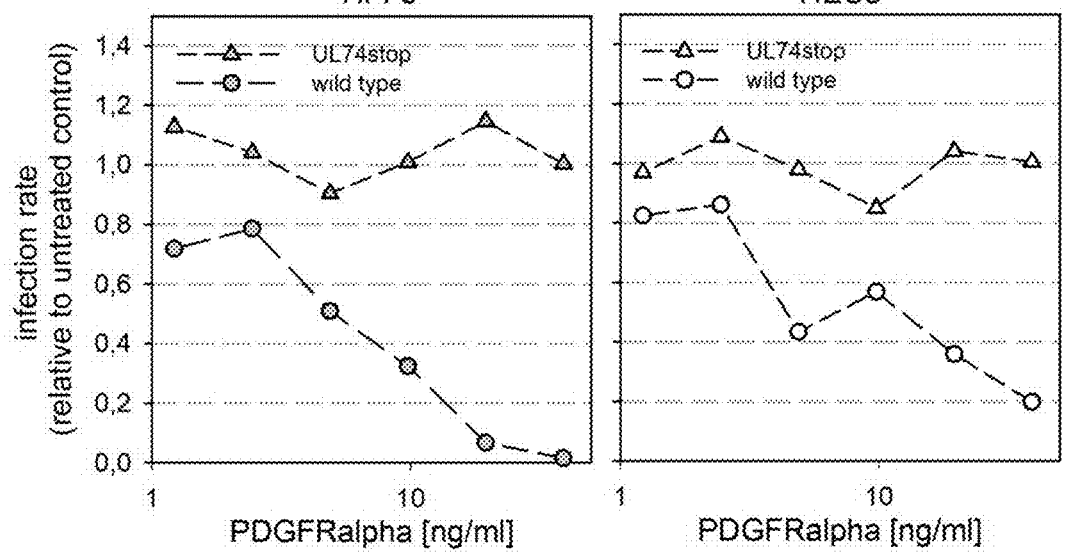

As a possible way of inactivation of HCMV, the inventors found that PDGFR-alpha-Fc binds the viral envelope glycoprotein pUL74. It was recently demonstrated that HCMV lacking pUL74 is deficient for fusion into host cells (42). To test whether pUL74 is an interaction partner of PDGFR-alpha-Fc, the inventors tested whether gO deficient particles can be stained with the soluble molecule similarly to wild type particles (shown in FIG. 8). HCMV wild type or UL74stop particles were incubated with 500 ng/ml PDGFR-alpha-Fc or PDGFRβ-Fc for 2 h before attachment to the cells ice. The particles on the cells were visualized with an antibody recognizing the structural protein pp150 and anti-human (FIG. 8A). Only virus particles containing the glycoprotein pUL74 were stained with the anti-human Fc antibody, indicating that the trimeric gH/gL/pUL74 complex is involved in binding of PDGFR-alpha-Fc to virions.

To further investigate this, inhibition assays were performed with the UL74stop virus (FIG. 8B). As deletion of pUL74 from the virus has a severe effect on infectivity, virions had to be 50 fold concentrated for the experiment, whereas wild type virus had to be diluted to achieve similar infection rates. The infectivity of the UL74stop virus did not significantly change with increasing doses of PDGFR-alpha-Fc, indicating that PDGFR-alpha-Fc might inhibit HCMV infection via blocking gH/gL/gO.

Example 12

Figure 9:
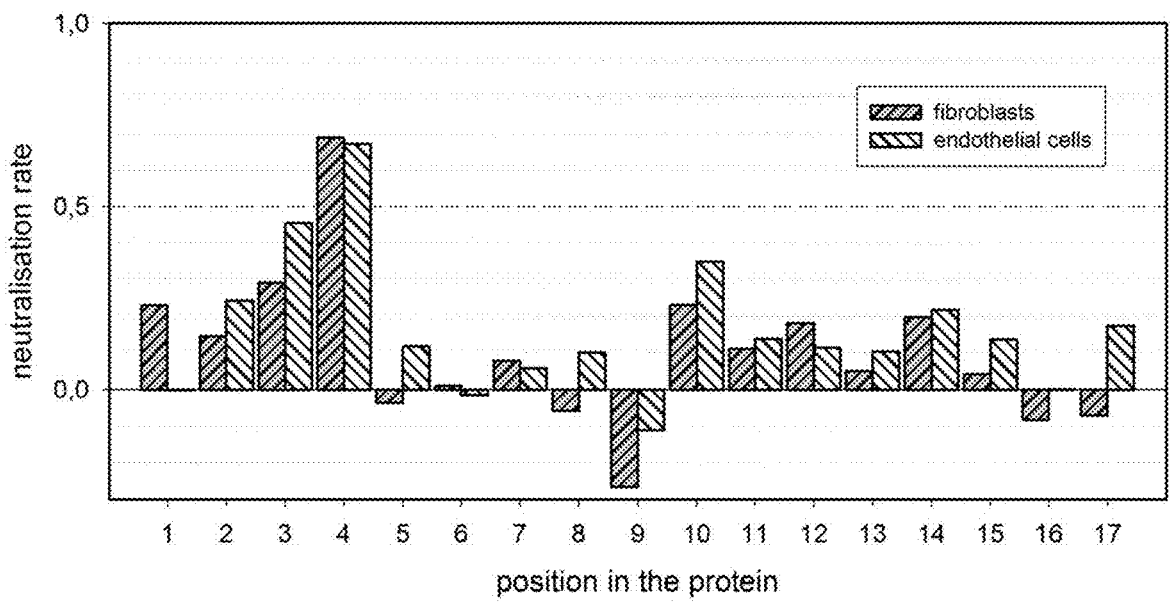
Figure 9:
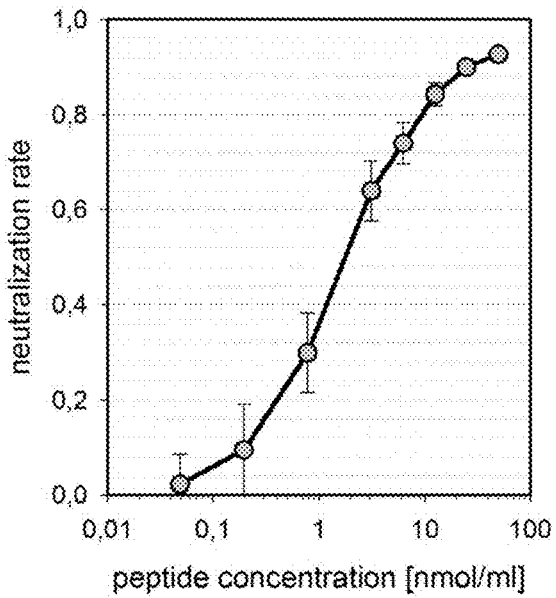
Figure 9:
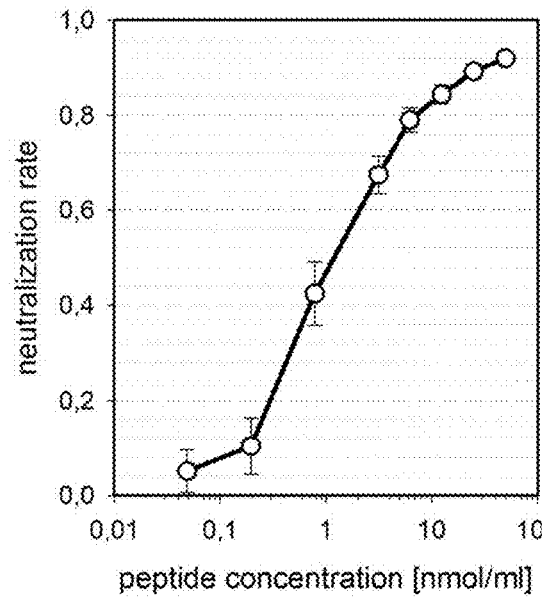

Peptides Derived from the Extracellular Domain of PDGFR-Alpha Inhibit HCMV Infection The surprising finding that only PDGFR-alpha-Fc but not EGFR-Fc or PDGFR-beta-Fc inhibits HCMV infection had indicated that the inhibitory effect is due to the PDGFR-alpha part of the chimeric molecule, which is actually only the extracellular domain of the native PDGFR-alpha transmembrane molecule. The inventors unexpectedly found that short peptides derived from this protein could also inhibit infection, and therefore tested a set of overlapping 40mer peptides covering the whole sequence of the extracellular PDGFR-alpha domain regarding the inhibitory potential of the individual peptides. Cell free preparations of strain TB40/E were pre-incubated with the individual peptides at concentrations reaching from 0.05-50 nmol/ml for 2 h and the mixtures were then incubated with HFF cultures in a 96-well format. The various peptides differed greatly regarding their inhibitory potential with a region between aa120 and aa280 being absolutely ineffective and the peptides surrounding this region having the highest anti-HCMV effect (FIG. 9). The peptide between aa90 and aa130 was particularly effective with an $EC_{50}$ of 2 nmol/ml an almost complete inhibition at 10 nmol/ml maximal inhibition.

Example 13

Quantification of the Inhibitory Potential of PDGFR-Alpha-Fc Variants with Small Deletions within the Proposed Ligand Binding Sites on HCMV Infection Deletion mutant PDGFR-alpha-Fc proteins set forth below and non-deleted PDGFR-alpha-Fc were expressed in 293T cells and purified using protein A. These proteins were initially diluted in cell culture medium to a concentration of 8000 ng/ml and were subsequently further diluted in a row of 2-fold dilutions to a minimum concentration of 4 ng/ml. In the inhibition assays, controls were used that contain the same amount of dilution medium and protein dilution buffer in order to rule out the occurrence of a non-specific inhibition of binding through the respective buffers. Diluted probes containing deletion mutants of PDGFR-alpha-Fc or whole PDGFR-alpha-Fc (without deletions) were mixed at a ratio of 1:1 with HCMV expressing luciferase and subsequently incubated for 2 h at 37° C. These mixtures were subsequently used in infection assays of human fibroblasts. After 2 h incubation of cells with the virus and respectively diluted deletion mutants or non-deleted PDGFR-alpha-Fc as control were removed from the cells and the cells were incubated for additional 24 h in cell culture medium. Thereafter, the activity of the luciferase was determined as a measure of the extent of infection. The background noise measured in the controls with probes containing no deletion mutants of PDGFR-alpha-Fc or without whole PDGFR-alpha-Fc were subtracted from the measurements with deletion mutants of PDGFR-alpha-Fc and whole PDGFR-alpha-Fc, respectively.

Experimental Design:

Cells: HFF at $1.5 \times 10^4$/well seeded the day before on 96-well flat bottom cell culture plates coated freshly with 0.1% gelatin Virus: BAC4 GLuc (yields 60-70% infection at 1:50 dilution; expresses *Gaussia* luciferase under control of the HCMV IE promotor)

Soluble Receptor:

Recombinant Human PDGFR alpha Fc Chimera and variants with small deletions within the predicted ligand binding sites. All Proteins were expressed in HEK 293T cells and purified using Protein A sepharose. The proteins were eluted in elution buffer (Thermo) with 10% 1 M Tris pH 8.

Treatment

Pre-Incubation of Virus with the Recombinant Proteins

For each recombinant Protein a 2-fold dilution series starting with 8 µg/ml was prepared. As a negative reference sample control dilution series containing the same volumes of Elution buffer were prepared. PDGFR-alpha-Fc serves as a positive control.

Total volume per dilution: 120 µl

|  | Protein conc. BCA (E2) [µg/ml] | % dilution for 8 µg/ml | Vol protein + buffer for 8 µg | Volume MEM5G |
| --- | --- | --- | --- | --- |
| delM133-I139 | 21.5 | 37.2 | 89.3 | 151 |
| del V184-G186 | 11.2 | 71.4 | 171.4 | 69 |
| del N204-208 | 80.9 | 9.9 | 23.7 | 216 |
| del242-247 | 20.6 | 38.8 | 93.2 | 147 |
| del261-264 | 16.2 | 49.4 | 118.5 | 121 |
| del272-275 | 17.5 | 45.7 | 109.7 | 130 |

-continued

| | Protein conc. BCA (E2) [µg/ml] | % dilution for 8 µg/ml | Vol protein + buffer for 8 µg | Volume MEM5G |
|---|---|---|---|---|
| del296-300 | 82.7 | 9.7 | 23.2 | 217 |
| PDGFR-alpha-Fc | 12.6 | 63.5 | 152.4 | 88 |

| Conc. [ng/ml] | 8000 | 4000 | 2000 | 1000 | 500 | 250 | 125 | 62.5 | 31.25 | 15.63 | 7.81 | 3.9 |
|---|---|---|---|---|---|---|---|---|---|---|---|---|

Figure 10:
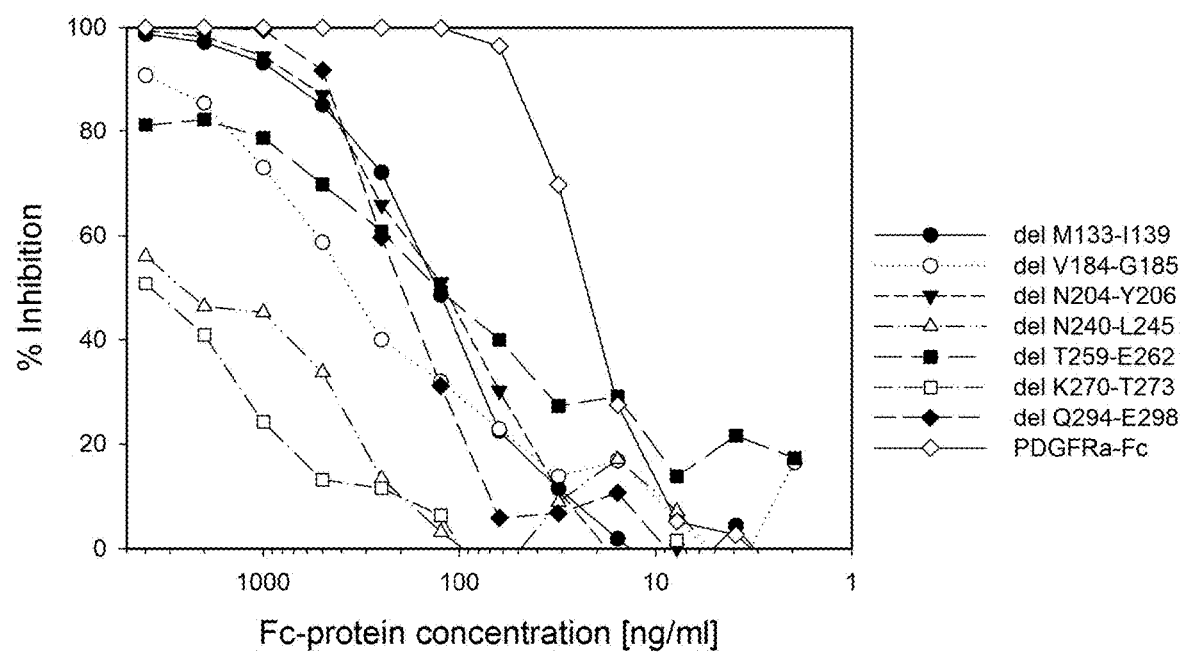

100 µl of each inhibitor dilution were mixed with 100 µl of HCMV BAC4Gluc (1:25 diluted)
⇒effective concentration of soluble receptor after addition of virus [ng/ml]:

| Conc. [ng/ml] | 4000 | 2000 | 1000 | 500 | 250 | 125 | 62.5 | 31.25 | 15.63 | 7.81 | 3.9 | 1.95 |
|---|---|---|---|---|---|---|---|---|---|---|---|---| incubate for 2 h at 37° C.
Infection:
Cell culture medium was replaced with the virus-receptor mixtures
Cultures were incubated for 2 h at 37° C.
After 2 h, virus was removed and replaced with medium.
Cultures were then incubated o/n.
Measurement of *Gaussia* Luciferase:
The Luciferase containing culture media was removed from the cells. A proportion (20 µl) was mixed with *Gaussia* substrate Coelenterazine and light emission was measured at 492 nm.
The light emission of samples treated with only buffer was subtracted from the values of the respective samples.
Cells were fixed with 80% acetone for 5 min at RT to allow for IE staining at a later time point.
The results of these experiments are shown in FIG. 10.

Example 14

Focus Expansion Assays with the Repaired Strain Merlin (Initial Infection with Supernatant)

Figure 11:
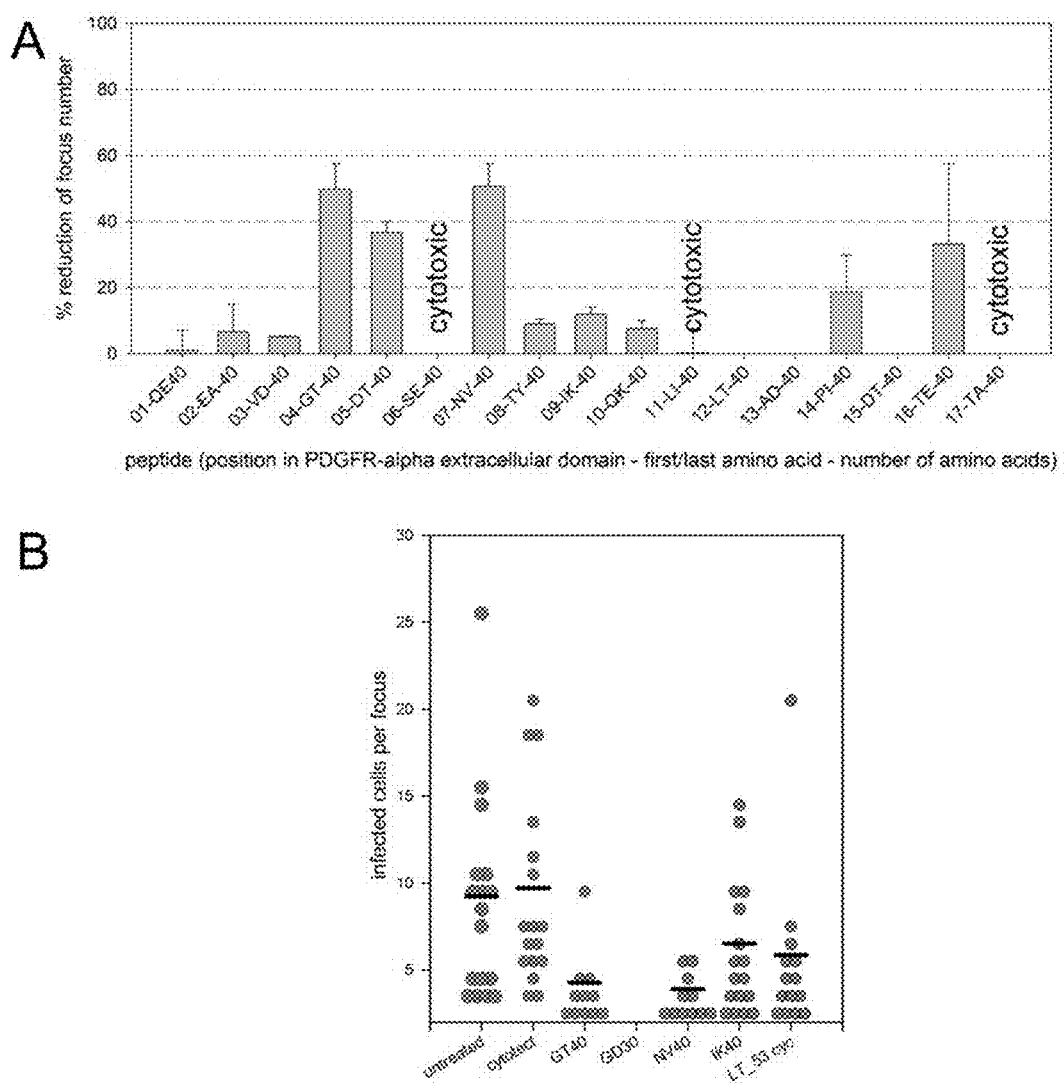

The effect of a substance of interest on viral spread is tested by a focus expansion assay essentially as previously described (Sinzger et al., 1997) with the following modifications. Instead of co-culturing infected with uninfected cells, indicator cells are directly infected with cell-free infectious preparations of the repaired strain Merlin (suitable for conditional expression of RL13 and UL128 L). HFFs (or other indicator cells of choice), seeded in gelatin-coated 96-well plates at a density of 15,000 cells/well are infected with a virus dose resulting in about 50 infected cells/well, and are subsequently cultured for 7 days in the presence or absence of the substance to be tested. Plates are then fixed with 80% acetone for 5 min at ambient temperature and stained for HCMV immediate-early antigen by indirect immunofluorescence using primary antibody E13 (Argene) and secondary antibody Cy3-goat anti-mouse IgG F(ab')$_2$ (Jackson ImmunoResearch). Nuclei of all cells are stained with DAPI. The number of infectious foci per well is counted; "infectious foci" being defined as clusters of at least three infected cells. In addition, the number of infected cells of randomly selected infectious foci is counted and "focus size" is given as infected cells/focus. The distribution of values for "focus size" is plotted for each combination of substance with one dot representing one focus, and virus and values of the central tendency (mean or median) are plotted in addition. The results are shown in FIG. 11.

Focus Expansion Assays with Clinical Isolates or Strain Merlin (Initial Infection by Coculture):

The effect of a substance of interest on viral spread is tested by a focus expansion assay essentially as previously described (Sinzger et al., 1997). Aliquots of infected cell cultures (HFFs or HFFF-tet cells with about 10% CPE) are thawed, washed with MEM and co-cultured with an 100-fold excess of uninfected indicator cells (e.g. fibroblasts, endothelial cells or epithelial cells) for 7 days in gelatin-coated 96-well plates in the presence or absence of the substance to be tested. Plates are then fixed with 80% acetone for 5 min at ambient temperature and stained for HCMV immediate-early antigen by indirect immunofluorescence using primary antibody E13 (Argene) and secondary antibody Cy3-goat anti-mouse IgG F(ab')2 (Jackson ImmunoResearch). Nuclei of all cells are stained with DAPI. The number of infectious foci per well is counted; "infectious foci" being defined as clusters of at least three infected cells. In addition, the number of infected cells of randomly selected infectious foci is counted and "focus size" is given as infected cells/focus. The distribution of values for "focus size" is plotted for each combination of substance with one dot representing one focus, and virus and values of the central tendency (mean or median) are plotted in addition.

REFERENCES

1. Adler, B., L. Scrivano, Z. Ruzcics, B. Rupp, C. Sinzger, and U. Koszinowski. 2006. Role of human cytomegalovirus UL131A in cell type-specific virus entry and release. The Journal of general virology 87:2451-2460.
2. Adler, B., and C. Sinzger. 2013. Cytomegalovirus Inter-Strain Variance in Cell-Type Tropism. In M. J. Reddehase (ed.), CYTOMEGALOVIRUSES: From Molecular Pathogenesis to Intervention, vol. 1. Caister Academic Press, Norfolk.
3. Ariza-Heredia, E. J., L. Nesher, and R. F. Chemaly. 2014. Cytomegalovirus diseases after hematopoietic stem cell transplantation: a mini-review. Cancer Lett 342:1-8.
4. Burke, H. G., and E. E. Heldwein. 2015. Crystal Structure of the Human Cytomegalovirus Glycoprotein B. PLoS Pathog 11:e1005227.
5. Ciferri, C., S. Chandramouli, A. Leitner, D. Donnarumma, M. A. Cianfrocco, R. Gerrein, K. Friedrich, Y. Aggarwal, G. Palladino, R. Aebersold, N. Norais, E. C. Settembre, and A. Carfi. 2015. Antigenic Characterization of the HCMV gH/gL/gO and Pentamer Cell Entry Complexes Reveals Binding Sites for Potently Neutralizing Human Antibodies. PLoS Pathog 11:e1005230.
6. Connolly, S. A., J. O. Jackson, T. S. Jardetzky, and R. Longnecker. 2011. Fusing structure and function: a structural view of the herpesvirus entry machinery. Nat Rev Microbiol 9:369-381.

7. Cranage, M. P., T. Kouzarides, A. T. Bankier, S. Satchwell, K. Weston, P. Tomlinson, B. Barrell, H. Hart, S. E. Bell, A. C. Minson, and et al. 1986. Identification of the human cytomegalovirus glycoprotein B gene and induction of neutralizing antibodies via its expression in recombinant vaccinia virus. EMBO J 5:3057-3063.
8. Cranage, M. P., G. L. Smith, S. E. Bell, H. Hart, C. Brown, A. T. Bankier, P. Tomlinson, B. G. Barrell, and T. C. Minson. 1988. Identification and expression of a human cytomegalovirus glycoprotein with homology to the Epstein-Barr virus BXLF2 product, varicella-zoster virus gpIII, and herpes simplex virus type 1 glycoprotein H. Journal of virology 62:1416-1422.
9. Eisenberg, R. J., D. Atanasiu, T. M. Cairns, J. R. Gallagher, C. Krummenacher, and G. H. Cohen. 2012. Herpes virus fusion and entry: a story with many characters. Viruses 4:800-832.
10. Falk, J. J., K. L. Sampaio, C. Stegmann, D. Lieber, B. Kropff, M. Mach, and C. Sinzger. 2016. Generation of a Gaussia luciferase-expressing endotheliotropic cytomegalovirus for screening approaches and mutant analyses. Journal of Virological Methods.
11. Feire, A. L., H. Koss, and T. Compton. 2004. Cellular integrins function as entry receptors for human cytomegalovirus via a highly conserved disintegrin-like domain. Proc. Natl. Acad. Sci. USA 101:15470-15475.
12. Fouts, A. E., P. Chan, J.-P. Stephan, R. Vandlen, and B. Feierbach. 2012. Antibodies against the gH/gL/UL128/UL130/UL131 Complex Comprise the Majority of the Anti-Cytomegalovirus (Anti-CMV) Neutralizing Antibody Response in CMV Hyperimmune Globulin. Journal of virology 86:7444-7447.
13. Gerna, G., A. Sarasini, M. Patrone, E. Percivalle, L. Fiorina, G. Campanini, A. Gallina, F. Baldanti, and M. G. Revello. 2008. Human cytomegalovirus serum neutralizing antibodies block virus infection of endothelial/epithelial cells, but not fibroblasts, early during primary infection. Journal of General Virology 89:853-865.
14. Goodfellow, I. G., D. J. Evans, A. M. Blom, D. Kerrigan, J. S. Miners, B. P. Morgan, and O. B. Spiller. 2005. Inhibition of coxsackie B virus infection by soluble forms of its receptors: binding affinities, altered particle formation, and competition with cellular receptors. Journal of virology 79:12016-12024.
15. Gwee, A., N. Curtis, T. G. Connell, S. Garland, and A. J. Daley. 2014. Ganciclovir for the treatment of congenital cytomegalovirus: what are the side effects? Pediatr Infect Dis J 33:115.
16. Hahn, G., M. G. Revello, M. Patrone, E. Percivalle, G. Campanini, A. Sarasini, M. Wagner, A. Gallina, G. Milanesi, U. Koszinowski, F. Baldanti, and G. Gerna. 2004. Human cytomegalovirus UL131-128 genes are indispensable for virus growth in endothelial cells and virus transfer to leukocytes. Journal of virology 78:10023-10033.
17. Haqqani, A. A., and J. C. Tilton. 2013. Entry inhibitors and their use in the treatment of HIV-1 infection. Antiviral Res 98:158-170.
18. Heldwein, E. E. 2016. gH/gL supercomplexes at early stages of herpesvirus entry. Curr Opin Virol 18:1-8.
19. Hirst, S. J., P. J. Barnes, and C. H. Twort. 1996. PDGF isoform-induced proliferation and receptor expression in human cultured airway smooth muscle cells. The American journal of physiology 270:L415-428.
20. Huber, M. T., and T. Compton. 1998. The human cytomegalovirus UL74 gene encodes the third component of the glycoprotein H-glycoprotein L-containing envelope complex. Journal of virology 72:8191-8197.
21. Isaacson, M. K., A. L. Feire, and T. Compton. 2007. Epidermal growth factor receptor is not required for human cytomegalovirus entry or signaling. J. Virol. 81:6241-6247.
22. Kaye, J. F., U. A. Gompels, and A. C. Minson. 1992. Glycoprotein H of human cytomegalovirus (HCMV) forms a stable complex with the HCMV UL115 gene product. The Journal of general virology 73 (Pt 10):2693-2698.
23. Kropff, B., M. P. Landini, and M. Mach. 1993. An ELISA using recombinant proteins for the detection of neutralizing antibodies against human cytomegalovirus. J Med Virol 39:187-195.
24. Li, L., J. A. Nelson, and W. J. Britt. 1997. Glycoprotein H-related complexes of human cytomegalovirus: identification of a third protein in the gCIII complex. Journal of virology 71:3090-3097.
25. Lieber, D., D. Hochdorfer, D. Stoehr, A. Schubert, R. Lotfi, T. May, D. Wirth, and C. Sinzger. 2015. A permanently growing human endothelial cell line supports productive infection with human cytomegalovirus under conditional cell growth arrest. Biotechniques 59:127-136.
26. Macagno, A., N. L. Bernasconi, F. Vanzetta, E. Dander, A. Sarasini, M. G. Revello, G. Gerna, F. Sallusto, and A. Lanzavecchia. 2010. Isolation of Human Monoclonal Antibodies That Potently Neutralize Human Cytomegalovirus Infection by Targeting Different Epitopes on the gH/gL/UL128-131A Complex. Journal of virology 84:1005-1013.
27. Mach, M., B. Kropff, P. Dal Monte, and W. Britt. 2000. Complex formation by human cytomegalovirus glycoproteins M (gpUL100) and N (gpUL73). Journal of virology 74:11881-11892.
28. May, T., M. Butueva, S. Bantner, D. Markusic, J. Seppen, R. A. MacLeod, H. Weich, H. Hauser, and D. Wirth. 2010. Synthetic gene regulation circuits for control of cell expansion. Tissue Eng Part A 16:441-452.
29. Pinkert, S., D. Westermann, X. Wang, K. Klingel, A. Dorner, K. Savvatis, T. Grossl, S. Krohn, C. Tschope, H. Zeichhardt, K. Kotsch, K. Weitmann, W. Hoffmann, H. P. Schultheiss, O. B. Spiller, W. Poller, and H. Fechner. 2009. Prevention of cardiac dysfunction in acute coxsackievirus B3 cardiomyopathy by inducible expression of a soluble coxsackievirus-adenovirus receptor. Circulation 120:2358-2366.
30. Planitzer, C. B., M. D. Saemann, H. Gajek, M. R. Farcet, and T. R. Kreil. 2011. Cytomegalovirus neutralization by hyperimmune and standard intravenous immunoglobulin preparations. Transplantation 92:267-270.
31. Rasmussen, L. E., R. M. Nelson, D. C. Kelsall, and T. C. Merigan. 1984. Murine monoclonal antibody to a single protein neutralizes the infectivity of human cytomegalovirus. Proc. Natl. Acad. Sci. USA 81:876-880.
32. Sinzger, C., G. Hahn, M. Digel, R. Katona, K. L. Sampaio, M. Messerle, H. Hengel, U. Koszinowski, W. Brune, and B. Adler. 2008. Cloning and sequencing of a highly productive, endotheliotropic virus strain derived from human cytomegalovirus TB40/E. The Journal of general virology 89:359-368.
33. Soroceanu, L., A. Akhavan, and C. S. Cobbs. 2008. Platelet-derived growth factor-alpha receptor activation is required for human cytomegalovirus infection. Nature 455:391-395.
34. Urban, S., R. Bartenschlager, R. Kubitz, and F. Zoulim. 2014. Strategies to inhibit entry of HBV and HDV into hepatocytes. Gastroenterology 147:48-64.

35. Vanarsdall, A. L., T. W. Wisner, H. Lei, A. Kazlauskas, and D. C. Johnson. 2012. PDGF receptor-alpha does not promote HCMV entry into epithelial and endothelial cells but increased quantities stimulate entry by an abnormal pathway. PLoS Pathog 8:e1002905.
36. Wang, D., F. Li, D. C. Freed, A. C. Finnefrock, A. Tang, S. N. Grimes, D. R. Casimiro, and T.-M. Fu. 2011. Quantitative analysis of neutralizing antibody response to human cytomegalovirus in natural infection. Vaccine 29:9075-9080.
37. Wang, D., and T. Shenk. 2005. Human cytomegalovirus UL131 open reading frame is required for epithelial cell tropism. Journal of virology 79:10330-10338.
38. Wang, X., D. Y. Huang, S.-M. Huong, and E.-S. Huang. 2005. Integrin alphavbeta3 is a coreceptor for human cytomegalovirus. Nat. Med. 11:515-521.
39. Wang, X., S.-M. Huong, M. L. Chiu, N. Raab-Traub, and E.-S. Huang. 2003. Epidermal growth factor receptor is a cellular receptor for human cytomegalovirus. Nature 424: 456-461.
40. Wassaf, D., G. Kuang, K. Kopacz, Q. L. Wu, Q. Nguyen, M. Toews, J. Cosic, J. Jacques, S. Wiltshire, J. Lambert, C. C. Pazmany, S. Hogan, R. C. Ladner, A. E. Nixon, and D. J. Sexton. 2006. High-throughput affinity ranking of antibodies using surface plasmon resonance microarrays. Analytical biochemistry 351:241-253.
41. Yanagawa, B., O. B. Spiller, D. G. Proctor, J. Choy, H. Luo, H. M. Zhang, A. Suarez, D. Yang, and B. M. McManus. 2004. Soluble recombinant coxsackievirus and adenovirus receptor abrogates coxsackievirus b3-mediated pancreatitis and myocarditis in mice. The Journal of infectious diseases 189:1431-1439.
42. Zhou, M., J. M. Lanchy, and B. J. Ryckman. 2015. Human Cytomegalovirus gH/gL/gO Promotes the Fusion Step of Entry into All Cell Types, whereas gH/gL/UL128-131 Broadens Virus Tropism through a Distinct Mechanism. Journal of virology 89:8999-9009.

Figure Description

FIG. 1: Effect of siRNA-mediated knockdown of growth factor receptors on infection efficiency in fibroblasts (A) and endothelial cells (B).

Figure 2:
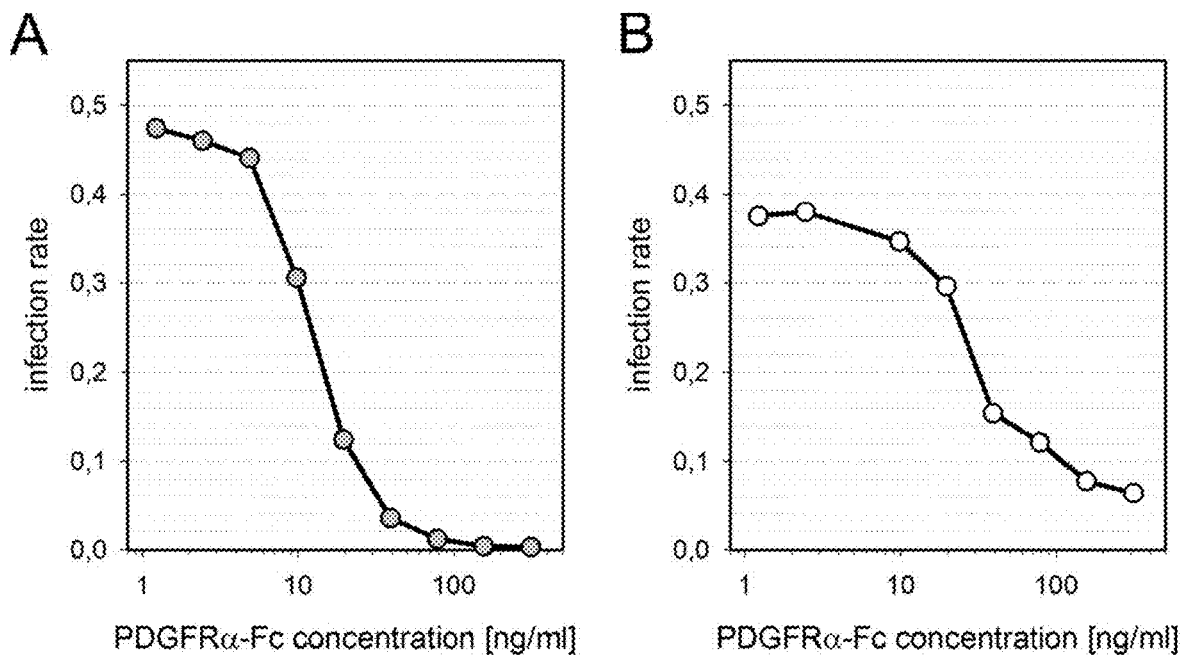

FIG. 2: Inhibitory effect of soluble PDGFR-alpha-Fc chimeras on HCMV infection of fibroblasts (A) and endothelial cells (B). Virus preparations of strain TB40/E were pretreated for 2 h with PDGFR-alpha at indicated concentrations and then added to cell cultures overnight. Cells were fixed and stained for viral IE antigens. Infections rates were calculated as the ratio of IE antigen-positive cells/total cell number.

Figure 3:
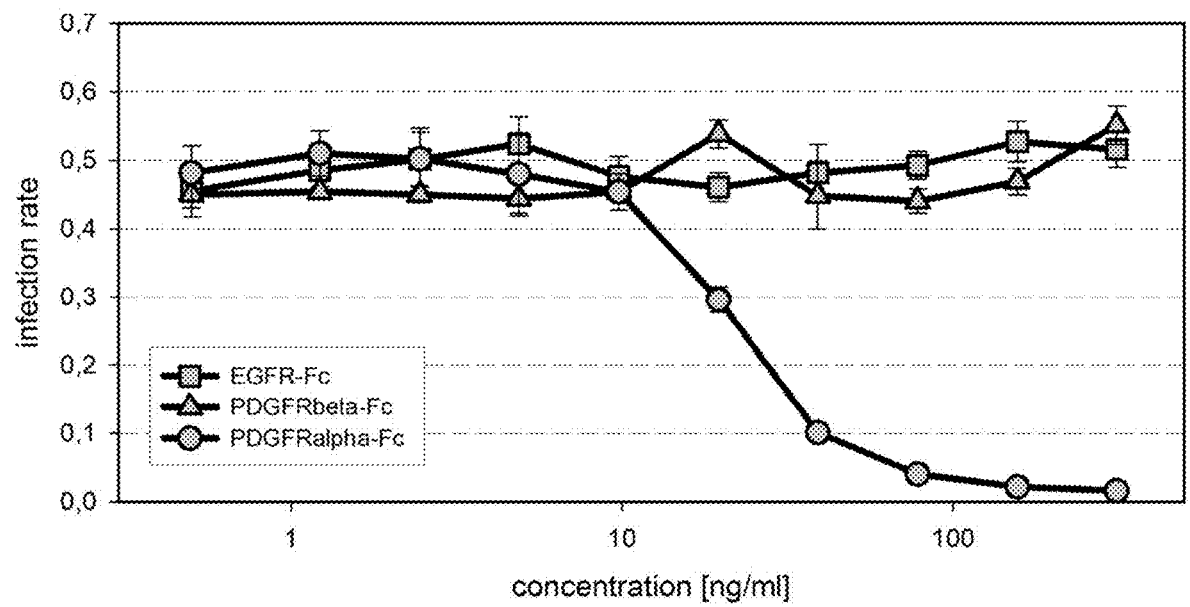
Figure 3:
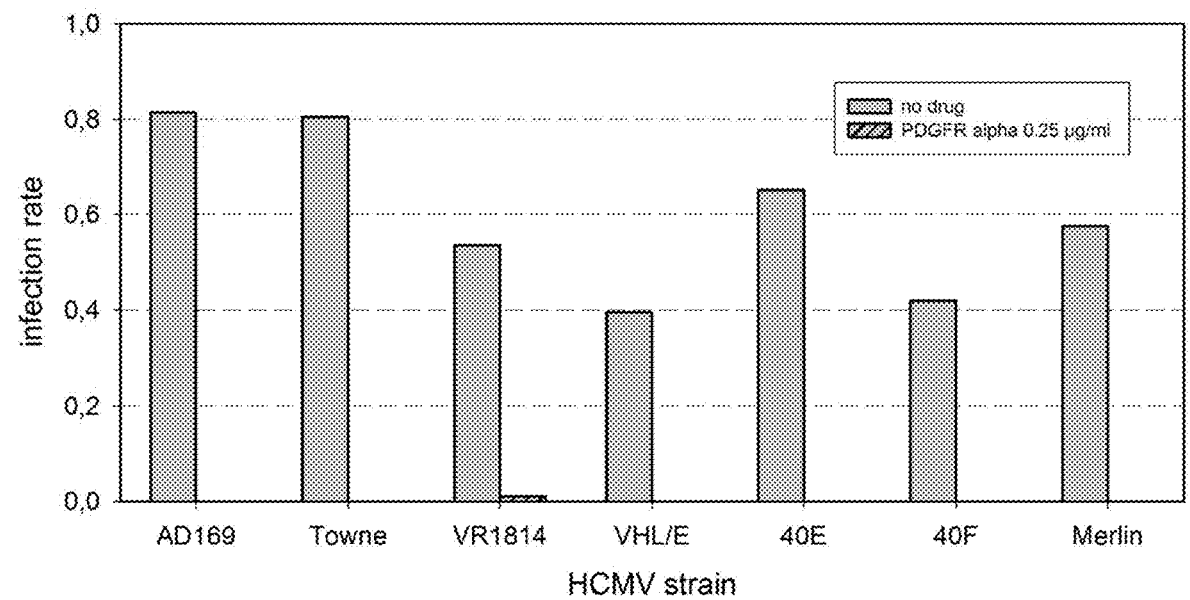

FIG. 3: The inhibitory effect of soluble PDGFR-alpha is specific and affects various HCMV strains. A: The soluble growth receptor molecules PDGFR-alpha-Fc, PDGFR-beta-Fc and EGFR-Fc were compared regarding their inhibitory potential on infection of HFFs by HCMV strain TB40/E. Virus preparations were pretreated for 2 h with the respective growth receptor at indicated concentrations and then added to cell cultures overnight. Cells were fixed and stained for viral IE antigens. Infections rates were calculated as the ratio of IE antigen-positive cells/total cell number. B: The potential of PDGFR-alpha-Fc to inhibit fibroblast infection with HCMV strains other than TB40/E was tested using a collection of strains that represent all known glycoprotein variants. Infectious supernatants of the different strains were diluted to ~MOI 1 in MEM. The virus preparations were either pre-incubated with MEM (no drug) or MEM containing 0.25 µg/ml PDGFR-alpha-Fc.

FIG. 4: Binding of soluble PDGFR-Fc chimeras to HCMV particles. Virus preparations of strain TB40/E were pretreated for 2 h with PDGFR-alpha-Fc, PDGFR-beta-Fc or EGFR-Fc and then incubated with the cells for 90 min on ice. Cells were fixed and stained for the viral structural protein pUL32 (red) and for Fc (green).

FIG. 5: Quantification of PDGFR-alpha-Fc binding to HCMV particles. Virus preparations of strain TB40/E were pre-incubated with various concentrations of PDGFR-alpha-Fc. Binding of the Fc-protein was assessed after the cells were incubated for 90 min with the virus/PDGFR-alpha-Fc mixture by staining for the viral structural protein pUL32 (red) and for Fc (green) followed by quantification of signal intensities. In a parallel experiment HFFs were incubated with the same mixture for 24 hours and stained for the viral immediate early antigens to determine the infection rates resulting from pretreatment with the different PDGFR-alpha-Fc concentrations.

FIG. 6: Effect of soluble PDGFR-alpha on adsorption and penetration of HCMV. Adsorption (A) and penetration (B) of virus particles to HFFs and HECs was analyzed by visualization of dual fluorescent HCMV particles after 2 h of pre-incubation with 100 ng/ml soluble Fc-chimeras. Adsorption was assessed by counting the total number of bound virus particles (pUL32 EGFP signals) after 2 h incubation with the cells (A). Penetration was assessed by counting the fraction of total virus particles that is lacking the envelope (pUL100 mCherry signal) (B). One representative experiment out of three is shown. C: Examples of microscopic images taken in HFFs.

FIG. 7: Post adsorption inhibitory effect of soluble PDGFR-alpha. Virus preparations were adsorbed to fibroblasts on ice, before 200 ng/ml PDGFR-alpha-Fc was added. After 2 h the cells were then either directly shifted to 37° C. or treated with the chemical fusogen PEG. The resulting infection rates were assessed by staining for the viral immediate early antigens. The mean values of 3 independent experiments are shown in A, error bars indicate SEM. Representative immunofluorescence images are shown in B.

FIG. 8: pUL74 is the viral interaction partner of PDGFR-alpha-Fc. Virus preparations of strain TB40-BAC4 or TB40-BAC4UL74stop were pretreated for 2 h with PDGFR-alpha-Fc. A: HFFs were fixed after 90 min of incubation with the virus-inhibitor mixture followed by staining for the viral structural protein pUL32 (red) and for Fc (green). B: Wild type or pUL74stop virus preparations were pre-incubated for 2 h with PDGFR-alpha-Fc before infection of HFFs or HECs was allowed. Wild type or UL74stop virus preparations were diluted or concentrated respectively to obtain similar infection rates. Infection rates were determined by calculation of the number of immediate early positive nuclei over total DAPI stained nuclei per image. Out of three independent experiments one is shown.

FIG. 9: Inhibitory effect of PDGFR-alpha-derived peptides: A: Neutralizing effect of 40mer peptides (3.125 nmol/ml) derived from the extracellular domain of PDGFR-alpha on infection of endothelial cells and fibroblasts. B, C: Dose response curves of peptide GT40 (position 4 in Panel A) in fibroblasts (B) and endothelial cells (C).

FIG. 10: Inhibitory potential of different PDGFR-alpha-Fc derivatives against HCMV infection of fibroblasts. The deletions target sites that were predicted to be involved in binding of PDGFR-alpha to PDGF-A or PDGF-B. PDGFR-alpha-Fc fusion proteins deleted at the indicated positions were diluted to different concentrations and preincubated with HCMV strain TB40-BAC4-IE-Gluc for 2 h before infection of HFFs. On the following day, infection was measured by addition of the luciferase substrate coelenterazine and detection of the resulting luminescence. The degree of inhibition is determined as the ratio of values obtained with the respective protein concentration to the values measured in samples without PDGFR-alpha-Fc derivatives. PDGFR-alpha-Fc serves as a positive control.

FIG. 11: Effect of peptides on cell-to-cell-spread of strain Merlin. Fibroblasts infected laboratory strain Merlin (with repaired RL13 and UL128L gene regions) were incubated for 7 days with the peptides as indicated at a concentration of 60 nmol/ml. Control cultures were untreated or incubated in the presence of hyperimmunoglobulin (cytotect 1/100, 0.5 mg plasma protein/ml). Monolayers were fixed, and infected cells were visualized by indirect immunofluorescence staining of HCMV immediate early antigens. (A) The number of infectious foci per well was counted, and the reduction of the focus number by the respective peptide is shown as compared to untreated control. Bars represent mean values of 2 independent experiments; error bars represent the standard error of the mean. (B) For selected peptides, the numbers of infected cells per focus were counted. The data from one out of two experiments (yielding similar results) is shown. One dot represents the number of infected cells of an individual focus. Bars indicate mean values of all foci. GD30 (SEQ ID No. 11) is a shortened version of GT40 (SEQ ID No. 12). NV40 corresponds to SEQ ID No. 13. LT53_cyc is a cyclic version of GT40.

Figure 12:
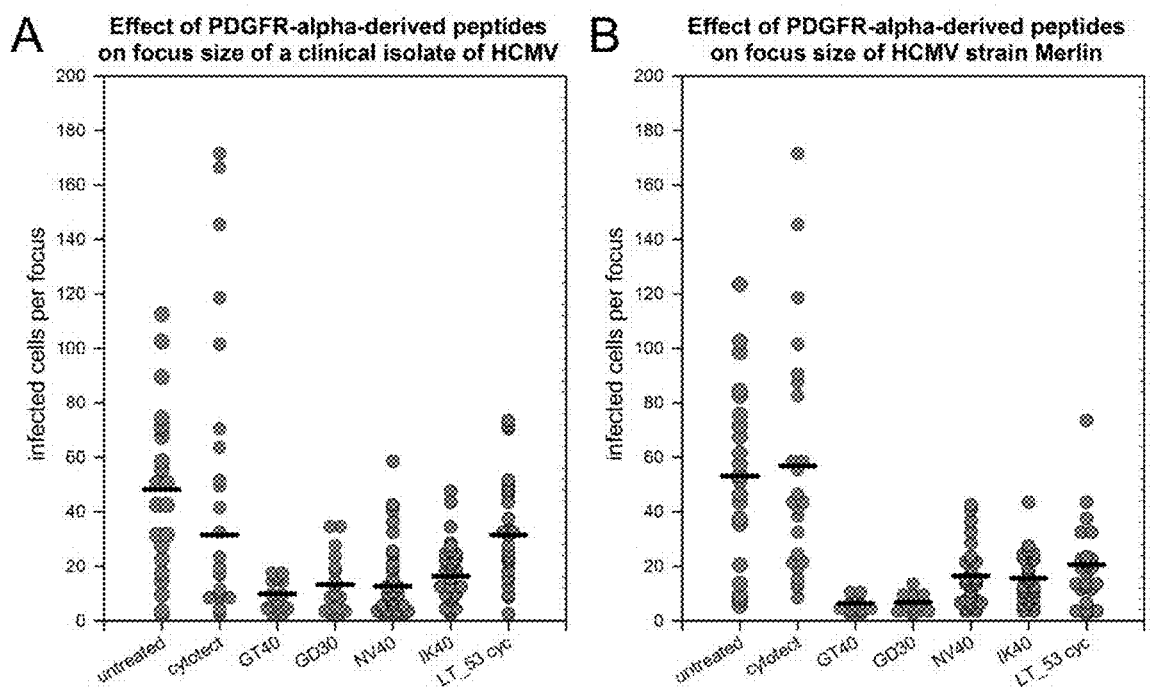

FIG. 12: Effect of peptides on cell-to-cell-spread of an HCMV clinical isolate. Fibroblasts infected by (A) clinical isolates and (B) laboratory strain Merlin (with repaired RL13 and UL128L gene regions) were co-cultured with a 100-fold excess of uninfected indicator fibroblasts for 7 days in the presence of peptides as indicated at a concentration of 60 nmol/ml. Control cultures were untreated or incubated in the presence of hyperimmunoglobulin (cytotect 1/100, 0.5 mg plasma protein/ml). Monolayers were fixed, and infected cells were visualitzed by indirect immunofluorescence staining of HCMV immediate early antigens. The numbers of infected cells per focus were counted. One dot represents the number of infected cells of an individual focus. Bars indicate mean values of all foci. GD30 (SEQ ID No. 11) is a shortened version of GT40 (SEQ ID No. 12). LT53 cyc is a cyclic version of GT40. NV40 corresponds to SEQ ID No. 13.

The invention claimed is:

1. A soluble PDGFR-alpha-Fc chimera consisting of the PDGFR-alpha sequence set forth in SEQ ID No. 2 and the amino sequence set forth in SEQ ID No. 8, wherein said chimera is capable of inhibiting HCMV entry.

2. A soluble PDGFR-alpha-Fc chimera consisting of a variant of the amino acid sequence set forth in SEQ ID No. 2 and the amino acid sequence set forth in SEQ ID No. 8, wherein said variant of the amino acid sequence set forth in SEQ ID No. 2 has one or more of the following deletions within SEQ ID No. 2 (numbering is adhered to SEQ ID No. 1):
   i) deletion of amino acids M133-I139;
   ii) deletion of amino acids V184-G185;
   iii) deletion of amino acids N204Y206;
   iv) deletion of amino acids T259-E262;
   v) deletion of amino acids Q294-E298;
   and wherein said chimera is capable of inhibiting HCMV entry.

3. A soluble PDGFR-alpha-Fc chimera consisting of a sequence selected from the group consisting of SEQ ID Nos: 3-7 and the amino sequence set forth in SEQ ID No. 8, wherein said chimera is capable of inhibiting HCMV entry.

4. The soluble PDGFR-alpha-Fc chimera as defined in claim 3, consisting of the amino acid sequence set forth in SEQ ID No. 3 and the amino acid sequence set forth in SEQ ID No. 8.

5. The soluble PDGFR-alpha-Fc chimera as defined in claim 3, consisting of the amino acid sequence set forth in SEQ ID No. 4 and the amino acid sequence set forth in SEQ ID No. 8.

6. The soluble PDGFR-alpha-Fc chimera as defined in claim 3, consisting of the amino acid sequence set forth in SEQ ID No. 5 and the amino acid sequence set forth in SEQ ID No. 8.

7. The soluble PDGFR-alpha-Fc chimera as defined in claim 3, consisting of the amino acid sequence set forth in SEQ ID No. 6 and the amino acid sequence set forth in SEQ ID No. 8.

8. The soluble PDGFR-alpha-Fc chimera as defined in claim 3, consisting of the amino acid sequence set forth in SEQ ID No. 7 and the amino acid sequence set forth in SEQ ID No. 8.

9. A PDGFR-alpha peptide fragment selected from the group consisting of:
   I. SEQ ID No. 9;
   II. SEQ ID No. 10;
   III. SEQ ID No. 11;
   IV. SEQ ID No. 12; and
   V. SEQ ID No. 13;
   wherein said fragment is capable of inhibiting HCMV entry.

* * * * *

SEQUENCE LISTING

```
<160> NUMBER OF SEQ ID NOS: 13

<210> SEQ ID NO 1
<211> LENGTH: 1089
<212> TYPE: PRT
<213> ORGANISM: Homo sapiens

<400> SEQUENCE: 1

Met Gly Thr Ser His Pro Ala Phe Leu Val Leu Gly Cys Leu Leu Thr
1               5                   10                  15

Gly Leu Ser Leu Ile Leu Cys Gln Leu Ser Leu Pro Ser Ile Leu Pro
            20                  25                  30

Asn Glu Asn Glu Lys Val Val Gln Leu Asn Ser Ser Phe Ser Leu Arg
        35                  40                  45

Cys Phe Gly Glu Ser Glu Val Ser Trp Gln Tyr Pro Met Ser Glu Glu
    50                  55                  60

Glu Ser Ser Asp Val Glu Ile Arg Asn Glu Glu Asn Asn Ser Gly Leu
65                  70                  75                  80

Phe Val Thr Val Leu Glu Val Ser Ser Ala Ser Ala Ala His Thr Gly
                85                  90                  95

Leu Tyr Thr Cys Tyr Tyr Asn His Thr Gln Thr Glu Glu Asn Glu Leu
            100                 105                 110

Glu Gly Arg His Ile Tyr Ile Tyr Val Pro Asp Pro Asp Val Ala Phe
        115                 120                 125

Val Pro Leu Gly Met Thr Asp Tyr Leu Val Ile Val Glu Asp Asp Asp
    130                 135                 140

Ser Ala Ile Ile Pro Cys Arg Thr Thr Asp Pro Glu Thr Pro Val Thr
145                 150                 155                 160

Leu His Asn Ser Glu Gly Val Val Pro Ala Ser Tyr Asp Ser Arg Gln
                165                 170                 175

Gly Phe Asn Gly Thr Phe Thr Val Gly Pro Tyr Ile Cys Glu Ala Thr
            180                 185                 190

Val Lys Gly Lys Lys Phe Gln Thr Ile Pro Phe Asn Val Tyr Ala Leu
        195                 200                 205

Lys Ala Thr Ser Glu Leu Asp Leu Glu Met Glu Ala Leu Lys Thr Val
    210                 215                 220
```

-continued

Tyr Lys Ser Gly Glu Thr Ile Val Val Thr Cys Ala Val Phe Asn Asn
225                 230                 235                 240

Glu Val Val Asp Leu Gln Trp Thr Tyr Pro Gly Glu Val Lys Gly Lys
            245                 250                 255

Gly Ile Thr Met Leu Glu Glu Ile Lys Val Pro Ser Ile Lys Leu Val
                260                 265                 270

Tyr Thr Leu Thr Val Pro Glu Ala Thr Val Lys Asp Ser Gly Asp Tyr
            275                 280                 285

Glu Cys Ala Ala Arg Gln Ala Thr Arg Glu Val Lys Glu Met Lys Lys
        290                 295                 300

Val Thr Ile Ser Val His Glu Lys Gly Phe Ile Glu Ile Lys Pro Thr
305                 310                 315                 320

Phe Ser Gln Leu Glu Ala Val Asn Leu His Glu Val Lys His Phe Val
                325                 330                 335

Val Glu Val Arg Ala Tyr Pro Pro Arg Ile Ser Trp Leu Lys Asn
            340                 345                 350

Asn Leu Thr Leu Ile Glu Asn Leu Thr Glu Ile Thr Thr Asp Val Glu
            355                 360                 365

Lys Ile Gln Glu Ile Arg Tyr Arg Ser Lys Leu Lys Leu Ile Arg Ala
370                 375                 380

Lys Glu Glu Asp Ser Gly His Tyr Thr Ile Val Ala Gln Asn Glu Asp
385                 390                 395                 400

Ala Val Lys Ser Tyr Thr Phe Glu Leu Leu Thr Gln Val Pro Ser Ser
                405                 410                 415

Ile Leu Asp Leu Val Asp Asp His His Gly Ser Thr Gly Gly Gln Thr
            420                 425                 430

Val Arg Cys Thr Ala Glu Gly Thr Pro Leu Pro Asp Ile Glu Trp Met
        435                 440                 445

Ile Cys Lys Asp Ile Lys Lys Cys Asn Asn Glu Thr Ser Trp Thr Ile
450                 455                 460

Leu Ala Asn Asn Val Ser Asn Ile Ile Thr Glu Ile His Ser Arg Asp
465                 470                 475                 480

Arg Ser Thr Val Glu Gly Arg Val Thr Phe Ala Lys Val Glu Glu Thr
                485                 490                 495

Ile Ala Val Arg Cys Leu Ala Lys Asn Leu Leu Gly Ala Glu Asn Arg
            500                 505                 510

Glu Leu Lys Leu Val Ala Pro Thr Leu Arg Ser Glu Leu Thr Val Ala
        515                 520                 525

Ala Ala Val Leu Val Leu Leu Val Ile Val Ile Ile Ser Leu Ile Val
        530                 535                 540

Leu Val Val Ile Trp Lys Gln Lys Pro Arg Tyr Glu Ile Arg Trp Arg
545                 550                 555                 560

Val Ile Glu Ser Ile Ser Pro Asp Gly His Glu Tyr Ile Tyr Val Asp
                565                 570                 575

Pro Met Gln Leu Pro Tyr Asp Ser Arg Trp Glu Phe Pro Arg Asp Gly
            580                 585                 590

Leu Val Leu Gly Arg Val Leu Gly Ser Gly Ala Phe Gly Lys Val Val
        595                 600                 605

Glu Gly Thr Ala Tyr Gly Leu Ser Arg Ser Gln Pro Val Met Lys Val
        610                 615                 620

Ala Val Lys Met Leu Lys Pro Thr Ala Arg Ser Ser Glu Lys Gln Ala
625                 630                 635                 640

```
Leu Met Ser Glu Leu Lys Ile Met Thr His Leu Gly Pro His Leu Asn
                645                 650                 655

Ile Val Asn Leu Leu Gly Ala Cys Thr Lys Ser Gly Pro Ile Tyr Ile
            660                 665                 670

Ile Thr Glu Tyr Cys Phe Tyr Gly Asp Leu Val Asn Tyr Leu His Lys
        675                 680                 685

Asn Arg Asp Ser Phe Leu Ser His His Pro Glu Lys Pro Lys Lys Glu
690                 695                 700

Leu Asp Ile Phe Gly Leu Asn Pro Ala Asp Glu Ser Thr Arg Ser Tyr
705                 710                 715                 720

Val Ile Leu Ser Phe Glu Asn Asn Gly Asp Tyr Met Asp Met Lys Gln
                725                 730                 735

Ala Asp Thr Thr Gln Tyr Val Pro Met Leu Glu Arg Lys Glu Val Ser
            740                 745                 750

Lys Tyr Ser Asp Ile Gln Arg Ser Leu Tyr Asp Arg Pro Ala Ser Tyr
        755                 760                 765

Lys Lys Lys Ser Met Leu Asp Ser Glu Val Lys Asn Leu Leu Ser Asp
770                 775                 780

Asp Asn Ser Glu Gly Leu Thr Leu Leu Asp Leu Leu Ser Phe Thr Tyr
785                 790                 795                 800

Gln Val Ala Arg Gly Met Glu Phe Leu Ala Ser Lys Asn Cys Val His
                805                 810                 815

Arg Asp Leu Ala Ala Arg Asn Val Leu Leu Ala Gln Gly Lys Ile Val
            820                 825                 830

Lys Ile Cys Asp Phe Gly Leu Ala Arg Asp Ile Met His Asp Ser Asn
        835                 840                 845

Tyr Val Ser Lys Gly Ser Thr Phe Leu Pro Val Lys Trp Met Ala Pro
850                 855                 860

Glu Ser Ile Phe Asp Asn Leu Tyr Thr Thr Leu Ser Asp Val Trp Ser
865                 870                 875                 880

Tyr Gly Ile Leu Leu Trp Glu Ile Phe Ser Leu Gly Gly Thr Pro Tyr
                885                 890                 895

Pro Gly Met Met Val Asp Ser Thr Phe Tyr Asn Lys Ile Lys Ser Gly
            900                 905                 910

Tyr Arg Met Ala Lys Pro Asp His Ala Thr Ser Glu Val Tyr Glu Ile
        915                 920                 925

Met Val Lys Cys Trp Asn Ser Glu Pro Glu Lys Arg Pro Ser Phe Tyr
930                 935                 940

His Leu Ser Glu Ile Val Glu Asn Leu Leu Pro Gly Gln Tyr Lys Lys
945                 950                 955                 960

Ser Tyr Glu Lys Ile His Leu Asp Phe Leu Lys Ser Asp His Pro Ala
                965                 970                 975

Val Ala Arg Met Arg Val Asp Ser Asp Asn Ala Tyr Ile Gly Val Thr
            980                 985                 990

Tyr Lys Asn Glu Glu Asp Lys Leu Lys Asp Trp Glu Gly Gly Leu Asp
        995                 1000                1005

Glu Gln Arg Leu Ser Ala Asp Ser Gly Tyr Ile Ile Pro Leu Pro
        1010                1015                1020

Asp Ile Asp Pro Val Pro Glu Glu Asp Leu Gly Lys Arg Asn
        1025                1030                1035

Arg His Ser Ser Gln Thr Ser Glu Glu Ser Ala Ile Glu Thr Gly
        1040                1045                1050

Ser Ser Ser Ser Thr Phe Ile Lys Arg Glu Asp Glu Thr Ile Glu
```

```
                1055                1060                1065
    Asp Ile Asp Met Met Asp Asp Ile Gly Ile Asp Ser Ser Asp Leu
                    1070                1075                1080

Val Glu Asp Ser Phe Leu
            1085

<210> SEQ ID NO 2
<211> LENGTH: 501
<212> TYPE: PRT
<213> ORGANISM: Homo sapiens

<400> SEQUENCE: 2

Gln Leu Ser Leu Pro Ser Ile Leu Pro Asn Glu Asn Glu Lys Val Val
1               5                   10                  15

Gln Leu Asn Ser Ser Phe Ser Leu Arg Cys Phe Gly Glu Ser Glu Val
                20                  25                  30

Ser Trp Gln Tyr Pro Met Ser Glu Glu Ser Ser Asp Val Glu Ile
            35                  40                  45

Arg Asn Glu Glu Asn Asn Ser Gly Leu Phe Val Thr Val Leu Glu Val
        50                  55                  60

Ser Ser Ala Ser Ala Ala His Thr Gly Leu Tyr Thr Cys Tyr Tyr Asn
65                  70                  75                  80

His Thr Gln Thr Glu Glu Asn Glu Leu Glu Gly Arg His Ile Tyr Ile
                85                  90                  95

Tyr Val Pro Asp Pro Asp Val Ala Phe Val Pro Leu Gly Met Thr Asp
            100                 105                 110

Tyr Leu Val Ile Val Glu Asp Asp Ser Ala Ile Ile Pro Cys Arg
        115                 120                 125

Thr Thr Asp Pro Glu Thr Pro Val Thr Leu His Asn Ser Glu Gly Val
    130                 135                 140

Val Pro Ala Ser Tyr Asp Ser Arg Gln Gly Phe Asn Gly Thr Phe Thr
145                 150                 155                 160

Val Gly Pro Tyr Ile Cys Glu Ala Thr Val Lys Gly Lys Lys Phe Gln
                165                 170                 175

Thr Ile Pro Phe Asn Val Tyr Ala Leu Lys Ala Thr Ser Glu Leu Asp
            180                 185                 190

Leu Glu Met Glu Ala Leu Lys Thr Val Tyr Lys Ser Gly Glu Thr Ile
        195                 200                 205

Val Val Thr Cys Ala Val Phe Asn Asn Glu Val Val Asp Leu Gln Trp
    210                 215                 220

Thr Tyr Pro Gly Glu Val Lys Gly Lys Gly Ile Thr Met Leu Glu Glu
225                 230                 235                 240

Ile Lys Val Pro Ser Ile Lys Leu Val Tyr Thr Leu Thr Val Pro Glu
                245                 250                 255

Ala Thr Val Lys Asp Ser Gly Asp Tyr Glu Cys Ala Ala Arg Gln Ala
            260                 265                 270

Thr Arg Glu Val Lys Glu Met Lys Lys Val Thr Ile Ser Val His Glu
        275                 280                 285

Lys Gly Phe Ile Glu Ile Lys Pro Thr Phe Ser Gln Leu Glu Ala Val
    290                 295                 300

Asn Leu His Glu Val Lys His Phe Val Val Glu Val Arg Ala Tyr Pro
305                 310                 315                 320

Pro Pro Arg Ile Ser Trp Leu Lys Asn Asn Leu Thr Leu Ile Glu Asn
                325                 330                 335
```

```
Leu Thr Glu Ile Thr Thr Asp Val Glu Lys Ile Gln Glu Ile Arg Tyr
                340                 345                 350

Arg Ser Lys Leu Lys Leu Ile Arg Ala Lys Glu Glu Asp Ser Gly His
            355                 360                 365

Tyr Thr Ile Val Ala Gln Asn Glu Asp Ala Val Lys Ser Tyr Thr Phe
        370                 375                 380

Glu Leu Leu Thr Gln Val Pro Ser Ser Ile Leu Asp Leu Val Asp Asp
385                 390                 395                 400

His His Gly Ser Thr Gly Gly Gln Thr Val Arg Cys Thr Ala Glu Gly
                405                 410                 415

Thr Pro Leu Pro Asp Ile Glu Trp Met Ile Cys Lys Asp Ile Lys Lys
            420                 425                 430

Cys Asn Asn Glu Thr Ser Trp Thr Ile Leu Ala Asn Asn Val Ser Asn
        435                 440                 445

Ile Ile Thr Glu Ile His Ser Arg Asp Arg Ser Thr Val Glu Gly Arg
            450                 455                 460

Val Thr Phe Ala Lys Val Glu Thr Ile Ala Val Arg Cys Leu Ala
465                 470                 475                 480

Lys Asn Leu Leu Gly Ala Glu Asn Arg Glu Leu Lys Leu Val Ala Pro
                485                 490                 495

Thr Leu Arg Ser Glu
            500

<210> SEQ ID NO 3
<211> LENGTH: 461
<212> TYPE: PRT
<213> ORGANISM: Homo sapiens

<400> SEQUENCE: 3

Gln Leu Ser Leu Pro Ser Ile Leu Pro Asn Glu Asn Glu Lys Val Val
1               5                   10                  15

Gln Leu Asn Ser Ser Phe Ser Leu Arg Cys Phe Gly Glu Ser Glu Val
            20                  25                  30

Ser Trp Gln Tyr Pro Met Ser Glu Glu Glu Ser Ser Asp Val Glu Ile
        35                  40                  45

Arg Asn Glu Glu Asn Asn Ser Gly Leu Phe Val Thr Val Leu Glu Val
    50                  55                  60

Ser Ser Ala Ser Ala Ala His Thr Gly Leu Tyr Thr Cys Tyr Tyr Asn
65                  70                  75                  80

His Thr Gln Thr Glu Glu Asn Glu Leu Glu Gly Arg His Ile Tyr Ile
                85                  90                  95

Tyr Val Pro Asp Pro Asp Val Ala Phe Val Pro Leu Gly Met Thr Asp
            100                 105                 110

Tyr Leu Val Ile Val Glu Asp Asp Ser Ala Ile Ile Pro Glu Ala
        115                 120                 125

Thr Val Lys Gly Lys Lys Phe Gln Thr Ile Pro Phe Asn Val Tyr Ala
    130                 135                 140

Leu Lys Ala Thr Ser Glu Leu Asp Leu Glu Met Glu Ala Leu Lys Thr
145                 150                 155                 160

Val Tyr Lys Ser Gly Glu Thr Ile Val Val Thr Cys Ala Val Phe Asn
                165                 170                 175

Asn Glu Val Val Asp Leu Gln Trp Thr Tyr Pro Gly Glu Val Lys Gly
            180                 185                 190

Lys Gly Ile Thr Met Leu Glu Glu Ile Lys Val Pro Ser Ile Lys Leu
        195                 200                 205
```

Val Tyr Thr Leu Thr Val Pro Glu Ala Thr Val Lys Asp Ser Gly Asp
    210                 215                 220

Tyr Glu Cys Ala Ala Arg Gln Ala Thr Arg Glu Val Lys Glu Met Lys
225                 230                 235                 240

Lys Val Thr Ile Ser Val His Glu Lys Gly Phe Ile Glu Ile Lys Pro
                245                 250                 255

Thr Phe Ser Gln Leu Glu Ala Val Asn Leu His Glu Val Lys His Phe
            260                 265                 270

Val Val Glu Val Arg Ala Tyr Pro Pro Arg Ile Ser Trp Leu Lys
        275                 280                 285

Asn Asn Leu Thr Leu Ile Glu Asn Leu Thr Glu Ile Thr Thr Asp Val
    290                 295                 300

Glu Lys Ile Gln Glu Ile Arg Tyr Arg Ser Lys Leu Lys Leu Ile Arg
305                 310                 315                 320

Ala Lys Glu Glu Asp Ser Gly His Tyr Thr Ile Val Ala Gln Asn Glu
                325                 330                 335

Asp Ala Val Lys Ser Tyr Thr Phe Glu Leu Leu Thr Gln Val Pro Ser
            340                 345                 350

Ser Ile Leu Asp Leu Val Asp Asp His His Gly Ser Thr Gly Gly Gln
        355                 360                 365

Thr Val Arg Cys Thr Ala Glu Gly Thr Pro Leu Pro Asp Ile Glu Trp
    370                 375                 380

Met Ile Cys Lys Asp Ile Lys Lys Cys Asn Asn Glu Thr Ser Trp Thr
385                 390                 395                 400

Ile Leu Ala Asn Asn Val Ser Asn Ile Ile Thr Glu Ile His Ser Arg
                405                 410                 415

Asp Arg Ser Thr Val Glu Gly Arg Val Thr Phe Ala Lys Val Glu Glu
            420                 425                 430

Thr Ile Ala Val Arg Cys Leu Ala Lys Asn Leu Leu Gly Ala Glu Asn
        435                 440                 445

Arg Glu Leu Lys Leu Val Ala Pro Thr Leu Arg Ser Glu
    450                 455                 460

<210> SEQ ID NO 4
<211> LENGTH: 416
<212> TYPE: PRT
<213> ORGANISM: Homo sapiens

<400> SEQUENCE: 4

Gln Leu Ser Leu Pro Ser Ile Leu Pro Asn Glu Asn Glu Lys Val Val
1               5                   10                  15

Gln Leu Asn Ser Ser Phe Ser Leu Arg Cys Phe Gly Glu Ser Glu Val
            20                  25                  30

Ser Trp Gln Tyr Pro Met Ser Glu Glu Glu Ser Ser Asp Val Glu Ile
        35                  40                  45

Arg Asn Glu Glu Asn Asn Ser Gly Leu Phe Val Thr Val Leu Glu Val
    50                  55                  60

Ser Ser Ala Ser Ala Ala His Thr Gly Leu Tyr Thr Cys Tyr Tyr Asn
65                  70                  75                  80

His Thr Gln Thr Glu Glu Asn Glu Leu Glu Gly Arg His Ile Tyr Ile
                85                  90                  95

Tyr Val Pro Asp Pro Asp Val Ala Phe Val Pro Leu Gly Met Thr Asp
            100                 105                 110

Tyr Leu Val Ile Val Glu Asp Asp Asp Ser Ala Ile Ile Pro Cys Ala

```
                115                 120                 125
Val Phe Asn Asn Glu Val Val Asp Leu Gln Trp Thr Tyr Pro Gly Glu
130                 135                 140

Val Lys Gly Lys Gly Ile Thr Met Leu Glu Glu Ile Lys Val Pro Ser
145                 150                 155                 160

Ile Lys Leu Val Tyr Thr Leu Thr Val Pro Glu Ala Thr Val Lys Asp
                165                 170                 175

Ser Gly Asp Tyr Glu Cys Ala Ala Arg Gln Ala Thr Arg Glu Val Lys
            180                 185                 190

Glu Met Lys Lys Val Thr Ile Ser Val His Glu Lys Gly Phe Ile Glu
        195                 200                 205

Ile Lys Pro Thr Phe Ser Gln Leu Glu Ala Val Asn Leu His Glu Val
    210                 215                 220

Lys His Phe Val Val Glu Val Arg Ala Tyr Pro Pro Pro Arg Ile Ser
225                 230                 235                 240

Trp Leu Lys Asn Asn Leu Thr Leu Ile Glu Asn Leu Thr Glu Ile Thr
                245                 250                 255

Thr Asp Val Glu Lys Ile Gln Glu Ile Arg Tyr Arg Ser Lys Leu Lys
            260                 265                 270

Leu Ile Arg Ala Lys Glu Glu Asp Ser Gly His Tyr Thr Ile Val Ala
        275                 280                 285

Gln Asn Glu Asp Ala Val Lys Ser Tyr Thr Phe Glu Leu Leu Thr Gln
    290                 295                 300

Val Pro Ser Ser Ile Leu Asp Leu Val Asp Asp His Gly Ser Thr
305                 310                 315                 320

Gly Gly Gln Thr Val Arg Cys Thr Ala Glu Gly Thr Pro Leu Pro Asp
                325                 330                 335

Ile Glu Trp Met Ile Cys Lys Asp Ile Lys Cys Asn Asn Glu Thr
            340                 345                 350

Ser Trp Thr Ile Leu Ala Asn Asn Val Ser Asn Ile Ile Thr Glu Ile
        355                 360                 365

His Ser Arg Asp Arg Ser Thr Val Glu Gly Arg Val Thr Phe Ala Lys
    370                 375                 380

Val Glu Glu Thr Ile Ala Val Arg Cys Leu Ala Lys Asn Leu Leu Gly
385                 390                 395                 400

Ala Glu Asn Arg Glu Leu Lys Leu Val Ala Pro Thr Leu Arg Ser Glu
                405                 410                 415

<210> SEQ ID NO 5
<211> LENGTH: 360
<212> TYPE: PRT
<213> ORGANISM: Homo sapiens

<400> SEQUENCE: 5

Gln Leu Ser Leu Pro Ser Ile Leu Pro Asn Glu Asn Glu Lys Val Val
1               5                   10                  15

Gln Leu Asn Ser Ser Phe Ser Leu Arg Cys Phe Gly Glu Ser Glu Val
            20                  25                  30

Ser Trp Gln Tyr Pro Met Ser Glu Glu Glu Ser Ser Asp Val Glu Ile
        35                  40                  45

Arg Asn Glu Glu Asn Asn Ser Gly Leu Phe Val Thr Val Leu Glu Val
    50                  55                  60

Ser Ser Ala Ser Ala Ala His Thr Gly Leu Tyr Thr Cys Tyr Tyr Asn
65                  70                  75                  80
```

```
His Thr Gln Thr Glu Glu Asn Glu Leu Glu Gly Arg His Ile Tyr Ile
                 85                  90                  95

Tyr Val Pro Asp Pro Asp Val Ala Phe Val Pro Leu Gly Met Thr Asp
            100                 105                 110

Tyr Leu Val Ile Val Glu Asp Asp Ser Ala Ile Ile Pro Ala Ala
            115                 120                 125

Arg Gln Ala Thr Arg Glu Val Lys Glu Met Lys Lys Val Thr Ile Ser
            130                 135                 140

Val His Glu Lys Gly Phe Ile Glu Ile Lys Pro Thr Phe Ser Gln Leu
145                 150                 155                 160

Glu Ala Val Asn Leu His Glu Val Lys His Phe Val Val Glu Val Arg
                165                 170                 175

Ala Tyr Pro Pro Arg Ile Ser Trp Leu Lys Asn Asn Leu Thr Leu
            180                 185                 190

Ile Glu Asn Leu Thr Glu Ile Thr Thr Asp Val Glu Lys Ile Gln Glu
                195                 200                 205

Ile Arg Tyr Arg Ser Lys Leu Lys Leu Ile Arg Ala Lys Glu Glu Asp
            210                 215                 220

Ser Gly His Tyr Thr Ile Val Ala Gln Asn Glu Asp Ala Val Lys Ser
225                 230                 235                 240

Tyr Thr Phe Glu Leu Leu Thr Gln Val Pro Ser Ser Ile Leu Asp Leu
                245                 250                 255

Val Asp Asp His His Gly Ser Thr Gly Gly Gln Thr Val Arg Cys Thr
            260                 265                 270

Ala Glu Gly Thr Pro Leu Pro Asp Ile Glu Trp Met Ile Cys Lys Asp
            275                 280                 285

Ile Lys Lys Cys Asn Asn Glu Thr Ser Trp Thr Ile Leu Ala Asn Asn
            290                 295                 300

Val Ser Asn Ile Ile Thr Glu Ile His Ser Arg Asp Arg Ser Thr Val
305                 310                 315                 320

Glu Gly Arg Val Thr Phe Ala Lys Val Glu Thr Ile Ala Val Arg
            325                 330                 335

Cys Leu Ala Lys Asn Leu Leu Gly Ala Glu Asn Arg Glu Leu Lys Leu
            340                 345                 350

Val Ala Pro Thr Leu Arg Ser Glu
            355                 360

<210> SEQ ID NO 6
<211> LENGTH: 126
<212> TYPE: PRT
<213> ORGANISM: Homo sapiens

<400> SEQUENCE: 6

Gln Leu Ser Leu Pro Ser Ile Leu Pro Asn Glu Asn Glu Lys Val Val
1               5                   10                  15

Gln Leu Asn Ser Ser Phe Ser Leu Arg Cys Phe Gly Glu Ser Glu Val
                20                  25                  30

Ser Trp Gln Tyr Pro Met Ser Glu Glu Glu Ser Ser Asp Val Glu Ile
            35                  40                  45

Arg Asn Glu Glu Asn Asn Ser Gly Leu Phe Val Thr Val Leu Glu Val
        50                  55                  60

Ser Ser Ala Ser Ala Ala His Thr Gly Leu Tyr Thr Cys Tyr Tyr Asn
65                  70                  75                  80

His Thr Gln Thr Glu Glu Asn Glu Leu Glu Gly Arg His Ile Tyr Ile
                85                  90                  95
```

```
Tyr Val Pro Asp Pro Asp Val Ala Phe Val Pro Leu Gly Met Thr Asp
                100                 105                 110

Tyr Leu Val Ile Val Glu Asp Asp Ser Ala Ile Ile Pro
            115                 120                 125
```

<210> SEQ ID NO 7
<211> LENGTH: 49
<212> TYPE: PRT
<213> ORGANISM: Homo sapiens

<400> SEQUENCE: 7

```
Tyr Tyr Asn His Thr Gln Thr Glu Glu Asn Glu Leu Glu Gly Arg His
1               5                   10                  15

Ile Tyr Ile Tyr Val Pro Asp Pro Asp Val Ala Phe Val Pro Leu Gly
            20                  25                  30

Met Thr Asp Tyr Leu Val Ile Val Glu Asp Asp Asp Ser Ala Ile Ile
        35                  40                  45

Pro
```

<210> SEQ ID NO 8
<211> LENGTH: 233
<212> TYPE: PRT
<213> ORGANISM: Artificial Sequence
<220> FEATURE:
<223> OTHER INFORMATION: Human Fc-sequence plus linker (Residues 1 to 6
      of SEQ ID NO. 1)

<400> SEQUENCE: 8

```
Leu Thr Val Ala Gly Ser Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220
```

```
Lys Ser Leu Ser Leu Ser Pro Gly Lys
225                 230
```

<210> SEQ ID NO 9
<211> LENGTH: 80
<212> TYPE: PRT
<213> ORGANISM: Homo sapiens

<400> SEQUENCE: 9

```
Val Leu Glu Val Ser Ser Ala Ser Ala Ala His Thr Gly Leu Tyr Thr
1               5                   10                  15

Cys Tyr Tyr Asn His Thr Gln Thr Glu Glu Asn Glu Leu Glu Gly Arg
            20                  25                  30

His Ile Tyr Ile Tyr Val Pro Asp Pro Asp Val Ala Phe Val Pro Leu
        35                  40                  45

Gly Met Thr Asp Tyr Leu Val Ile Val Glu Asp Asp Ser Ala Ile
50                  55                  60

Ile Pro Cys Arg Thr Thr Asp Pro Glu Thr Pro Val Thr Leu His Asn
65                  70                  75                  80
```

<210> SEQ ID NO 10
<211> LENGTH: 40
<212> TYPE: PRT
<213> ORGANISM: Artificial Sequence
<220> FEATURE:
<223> OTHER INFORMATION: Synthetic peptide

<400> SEQUENCE: 10

```
Ile Lys Val Pro Ser Ile Lys Leu Val Tyr Thr Leu Thr Val Pro Glu
1               5                   10                  15

Ala Thr Val Lys Asp Ser Gly Asp Tyr Glu Cys Ala Ala Arg Gln Ala
            20                  25                  30

Thr Arg Glu Val Lys Glu Met Lys
        35                  40
```

<210> SEQ ID NO 11
<211> LENGTH: 30
<212> TYPE: PRT
<213> ORGANISM: Artificial Sequence
<220> FEATURE:
<223> OTHER INFORMATION: Synthetic peptide

<400> SEQUENCE: 11

```
Gly Arg His Ile Tyr Ile Tyr Val Pro Asp Pro Asp Val Ala Phe Val
1               5                   10                  15

Pro Leu Gly Met Thr Asp Tyr Leu Val Ile Val Glu Asp Asp
            20                  25                  30
```

<210> SEQ ID NO 12
<211> LENGTH: 40
<212> TYPE: PRT
<213> ORGANISM: Artificial Sequence
<220> FEATURE:
<223> OTHER INFORMATION: Synthetic peptide

<400> SEQUENCE: 12

```
Gly Arg His Ile Tyr Ile Tyr Val Pro Asp Pro Asp Val Ala Phe Val
1               5                   10                  15

Pro Leu Gly Met Thr Asp Tyr Leu Val Ile Val Glu Asp Asp Ser
            20                  25                  30

Ala Ile Ile Pro Cys Arg Thr Thr
        35                  40
```

```
<210> SEQ ID NO 13
<211> LENGTH: 40
<212> TYPE: PRT
<213> ORGANISM: Artificial Sequence
<220> FEATURE:
<223> OTHER INFORMATION: Synthetic sequence

<400> SEQUENCE: 13

Asn Val Tyr Ala Leu Lys Ala Thr Ser Glu Leu Asp Leu Glu Met Glu
1               5                   10                  15

Ala Leu Lys Thr Val Tyr Lys Ser Gly Glu Thr Ile Val Val Thr Cys
                20                  25                  30

Ala Val Phe Asn Asn Glu Val Val
                35                  40
```